US012630587B2

(12) United States Patent
Schäberle et al.

(10) Patent No.: US 12,630,587 B2
(45) Date of Patent: May 19, 2026

(54) ANTIBIOTIC SELECTIVELY KILLS GRAM-NEGATIVE PATHOGENS

(71) Applicant: JUSTUS-LIEBIG-UNIVERSITAET GIESSEN, Giessen (DE)

(72) Inventors: Till Schäberle, Giessen (DE); Zerlina G. Wuisan, Giessen (DE); Nils Böhringer, Engelskirchen (DE); Luis J. Linares-Otoya, Giessen (DE)

(73) Assignee: JUSTUS-LIEBIG-UNIVERSITAET GIESSEN, Giessen (DE)

( * ) Notice: Subject to any disclaimer, the term of this patent is extended or adjusted under 35 U.S.C. 154(b) by 909 days.

(21) Appl. No.: 17/778,785

(22) PCT Filed: Nov. 20, 2020

(86) PCT No.: PCT/EP2020/025531
§ 371 (c)(1),
(2) Date: May 20, 2022

(87) PCT Pub. No.: WO2021/098989
PCT Pub. Date: May 27, 2021

(65) Prior Publication Data
US 2023/0348539 A1      Nov. 2, 2023

(30) Foreign Application Priority Data
Nov. 20, 2019     (EP) ..................................... 19210353

(51) Int. Cl.
*C07K 7/64*        (2006.01)
*C12N 15/74*        (2006.01)
(52) U.S. Cl.
CPC ................ *C07K 7/64* (2013.01); *C12N 15/74* (2013.01); *C12N 2800/101* (2013.01)
(58) Field of Classification Search
None
See application file for complete search history.

(56) References Cited

FOREIGN PATENT DOCUMENTS

WO        WO-2020018173 A1 *    1/2020    ............. A61K 38/08

OTHER PUBLICATIONS

Hersh et al, Clinical Infectious Diseases 2012;54(11):1677-8 (Year: 2012).*
International Search Report and Written Opinion for Application No. PCT/EP2020/025531, mailed Mar. 3, 2021.
Ye Ying et al., "Heterologous production of asperipin-2a: proposal for sequential oxidative macrocyclization by a fungi-specific DUF3328 oxidase", *Organic & Biomolecular Chemistry*, vol. 17, No. 1, pp. 39-43 (2018).
Graham A Hudson et al., "RiPP antibiotics: biosynthesis and engineering potential", *Current Opinion in Microbiology*, vol. 45, pp. 61-69 (2018).
Eva Vogt et al., "Discovery of novel fungal RiPP biosynthetic pathways and their application for the development of peptide therapeutics", *Applied Microbiology and Biotechnology*, vol. 103, No. 14, pp. 5567-5581 (2019).

* cited by examiner

*Primary Examiner* — Sergio Coffa
(74) *Attorney, Agent, or Firm* — MARSHALL, GERSTEIN & BORUN LLP

(57)        ABSTRACT

The invention is concerning a medical preparation comprising bicyclic heptapeptides for use in vertebrates or humans suffering from an infection caused by Gram-negative bacteria like *Pseudomonas aeruginosa, Klebsiella pneumoniae, Acineto-bacter baumannii, Neisseria gonorrhoeae, Chlamydia trachomatis, Shigella sonnei, Salmonella enterica Typhimurium* LT2, Enterobacter spp., *Bifidobacterium longum, Bacteroides fragilis, Lactobacillus reuteri, Enterococcus* spp., *Yersinia pestis* and numerous other Gram-negative bacteria.

13 Claims, 22 Drawing Sheets
Specification includes a Sequence Listing.

Darobactin A

Fig. 2B

Leader          Core          Tail

Trp-Lys and Trp-O-Trp
crosslinks are installed

Final trimming
and secretion

Trp Asn Trp Ser Lys Ser Phe

Fig. 2C

| | |
|---|---|
| *Photorhabdus temperata* HGB1456 | MHNTSIINCTTQEALNSLAASFKDTELSITERALDELNNKPKIPEITAWNWSKSFQEI* |
| *Photorhabdus khanii* DSM3369 | MHNTLNETVKTQEALNSLAASFKETELSITDKALNELSNKPKIPEITAWNWSKSFQEI* |
| *Photorhabdus australis* PB68.1 | MQNTLVETCKTQEALNSLAASFKETELSITEKALNELSSKPKIPEITAWNWSKSFQEI* |
| *Photorhabdus laumondii* BOJ-47 | MHNTSIINCTTQEALNSLAASFKDTELSITERALDELNNKPKIPEITAWNWSKSFQEI* |
| *Yersinia frederiksenii* ATCC 33641 | MHTSHQPDKKTGNTHLITLKTKLESLEESFKNSSLSINDHEIESLKNSDSDNKITAWNWSKSFTQQ* |
| *Vibrio tasmaniensis* 10N.222.51.A7 | MIIVEKEKVSISERLDALMSSFSEMNLELTKFDQEQVNSINIAPPITAWNWSKSF* |
| *Pseudoalteromonas luteaviolacea* S4054 | MIVEAPKEKVSISEKLDALKSSFSNQTLNIANVDQARVDSISVAPPITAWNWSKSFEK* |

| No. | δ H [ppm] | Multi-plicity | J [Hz] | Integral | δ C [ppm] | Signal phase HSQC | COSY coupling with No. | TOCSY coupling with No. | Assignment of CH | HMBC coupling with | Assignment of $C_q$ (and CH) |
|---|---|---|---|---|---|---|---|---|---|---|---|
| 1 | 7.90 | s | / | 1H | 128.88 | + | / | / | Trp 45 | 141.58 | Trp 43 |
|  |  |  |  |  |  |  |  |  |  | 129.28 | Trp 38 |
|  |  |  |  |  |  |  |  |  |  | 116.09 | Trp 37 |
| 2 | 7.53 – 7.45 | m | / | 4H | 133.23 | + | 3, 6 | 3, 6 | Phe 64 | 141.58 | Trp 43 |
|  |  |  |  |  |  |  |  |  |  | 141.07 | Phe 62 |
|  |  |  |  |  |  |  |  |  |  | 137.41 | Trp 41 |
|  |  |  |  |  |  |  |  |  |  | 133.23 | Phe 64 |
|  |  |  |  |  |  |  |  |  |  | 129.28 | Trp 38 |
|  |  |  |  |  | 121.87 | + |  |  | Trp 39 | 116.09 | Trp 37 |
|  |  |  |  |  | 114.95 | + |  |  | Trp 42 | 52.40 | Lys 49 |
| 3 | 7.43 – 7.36 | m | / | 4H | 133.86 | + | 2 | 2 | Phe 63 | 133.86 | Phe 63 |
|  |  |  |  |  |  |  |  |  |  | 133.50 or/and | Trp 30 or/and |
|  |  |  |  |  |  |  |  |  |  | 133.46 | Trp 25 |
|  |  |  |  |  | 131.65 | + |  |  | Phe 65 | 131.65 | Phe 65 |
|  |  |  |  |  | 129.15 | + |  |  | Trp 32 | 112.56 | Trp 24 |
|  |  |  |  |  |  |  |  |  |  | (40.99) | Phe 61 |
| 4 | 7.30 | t (roof ef-fect) | 7.29 | 2H | 118.24 | + | 5 | / | Trp 26 + Trp 28 | 149.59 | Trp 29 |
|  |  |  |  |  |  |  |  |  |  | 133.50 | Trp 30 |
|  |  |  |  |  |  |  |  |  |  | (118.24) | Trp 26 + Trp 28 |
|  |  |  |  |  | 113.45 | + |  |  |  | 113.45 |  |

Fig. 4 (continued)

| No. | δ H [ppm] | Multiplicity | J [Hz] | Integral | δ C [ppm] | Signal phase HSQC | COSY coupling with No. | TOCSY coupling with No. | Assignment of CH | HMBC coupling with | Assignment of $C_q$ (and CH) |
|---|---|---|---|---|---|---|---|---|---|---|---|
| 5 | 7.24 | t (roof effect) | 7.74 | 1H | 124.68 | + | 4 | / | Trp 27 | 149.59<br>133.46 | Trp 29<br>Trp 25 |
| 6 | 7.00<br>6.98 | d<br>d | 1.08<br>0.90 | 1H | 129.34 | + | 2 | 2 | Trp 40 | 129.28<br>114.95<br>52.40 | Trp 38<br>Trp 42<br>Lys 49 |
| 7 | 6.24 | d | 8.94 | 1H | 81.34 | + | 9 | 9 | Trp 36 | 149.59<br>128.88<br>116.09 | Trp 29<br>Trp 45<br>Trp 37 |
| 8 | 4.77 | dd | 5.67<br>9.03 | 2H (expected: 1H) | 58.52 | + | 18, 19 | 18, 19 | Phe 20 | 178.98<br>177.43<br>141.07<br>40.99 | Phe 21<br>Arg 18<br>Phe 62<br>Phe 61 |
| 9 | 4.74 | d | 9.00 | 1H | 67.81 | + | 7 | 7 | Trp 8 | 172.97<br>172.59<br>81.34 | Asn 6<br>Trp 9<br>Trp 36 |
| 10 | 4.34 | dd | 6.12<br>8.52 | 1H | 57.81 | + | (26), 27 | 20, (26), 27, 28 | Arg 17 | 177.43<br>175.85<br>32.73<br>(28.83) | Arg 18<br>Lys 15<br>Arg 54<br>Arg 55 |

Fig. 4 (continued)

| No. | δ H [ppm] | Multiplicity | J [Hz] | Integral | δ C [ppm] | Signal phase HSQC | COSY coupling with No. | TOCSY coupling with No. | Assignment of CH | HMBC coupling with | Assignment of $C_q$ (and CH) |
|---|---|---|---|---|---|---|---|---|---|---|---|
| 11 | 4.22 | d | 10.56 | 1H | 64.51 | + | 21 | 21, 23, 24, 25, 27 | Lys 14 | 175.85; 172.40; 52.40; (30.13) | Lys 15; Thr 12; Lys 49; Lys 50 |
| 12 | 4.08 | dd | 7.29 10.95 | 1H | 59.11 | + | 14, 17 | 14, 17 | Trp 2 | 172.64; 30.72 | Trp 3; Trp 23 |
| 13 | 3.77 | d | 6.48 | 1H | 62.52 | + | 15 | 15, 29 | Thr 11 | 172.59 or/ and; 172.40; 72.46; 22.73 | Trp 9 or/ and; Thr 12; Thr 46; Thr 47 |
| 14 | 3.60 | dd | 7.20 13.68 | 1H | 30.72 | - | 12, 17 | 12, 17 | Trp 23 | 172.64; 133.46; 112.56; 59.11 | Trp 3; Trp 25; Trp 24; Trp 2 |
| 15 | 3.43 | p (quin-tett) | 6.38 | 1H | 72.46 | + | 13, 29 | 13, 29 | Thr 46 | / | / |
| 16 | 3.37 | t | 6.84 | 2H (expected: 1H) | 55.19 | + | 22 | 22 | Asn 5 | 178.12; 172.97; 172.64; 43.29 | Asn 34; Asn 6; Trp 3; Asn 33 |

Fig. 4 (continued)

| No. | δ H [ppm] | Multi-plicity | J [Hz] | Integral | δ C [ppm] | Signal phase HSQC | COSY coupling with No. | TOCSY coupling with No. | Assignment of CH | HMBC coupling with | Assignment of Cq (and CH) |
|---|---|---|---|---|---|---|---|---|---|---|---|
| 17 | 3.35 | d | 12.00 (rev: 12.94) | 1H | 30.72 | - | 12, 14 | 12, 14 | Trp 23 | 112.56<br>59.11 | Trp 24<br>Trp 2 |
| 18 | 3.33 | dd | 5.16<br>13.90 | 1H | 40.99 | - | 8, 19 | 8, 19 | Phe 61 | 178.98<br>141.07<br>133.86<br>58.52 | Phe 21<br>Phe 62<br>Phe 63<br>Phe 20 |
| 19 | 3.17 | d | 8.88 | 1H | 40.99 | - | 8, 18 | 8, 18 | Phe 61 | 178.98<br>141.07<br>133.86<br>58.52 | Phe 21<br>Phe 62<br>Phe 63<br>Phe 20 |
| 20 | 3.14 | t | 7.20 | 2H | 44.88 | - | 28 | 10, 26, 27, 28 | Arg 56 | 161.13<br>32.73<br>28.83 | Arg 58<br>Arg 54<br>Arg 55 |
| 21 | 3.10 – 3.00 | m | / | 4H (expected: 3H) | 52.40<br>43.84 | +<br>- | 11, 23, 24, 25, (27) | 11, 23, 24, 25, 27 | Lys 49<br>Lys 52 | / | / |
| 22 | 2.21<br>2.21 | q<br>q | 12.79<br>8.18 | 2H | 43.29 | - | 16 | 16 | Asn 33 | 178.12<br>172.97<br>55.19 | Asn 34<br>Asn 6<br>Asn 5 |
| 23 | 2.16 – 2.09 | m | / | 1H | 30.13 or 30.01 | -<br>- | 21, (24), 25, 27 | 11, 21, 24, 25, 27 | Lys 50 or Lys 51 | / | / |

Fig. 4 (continued)

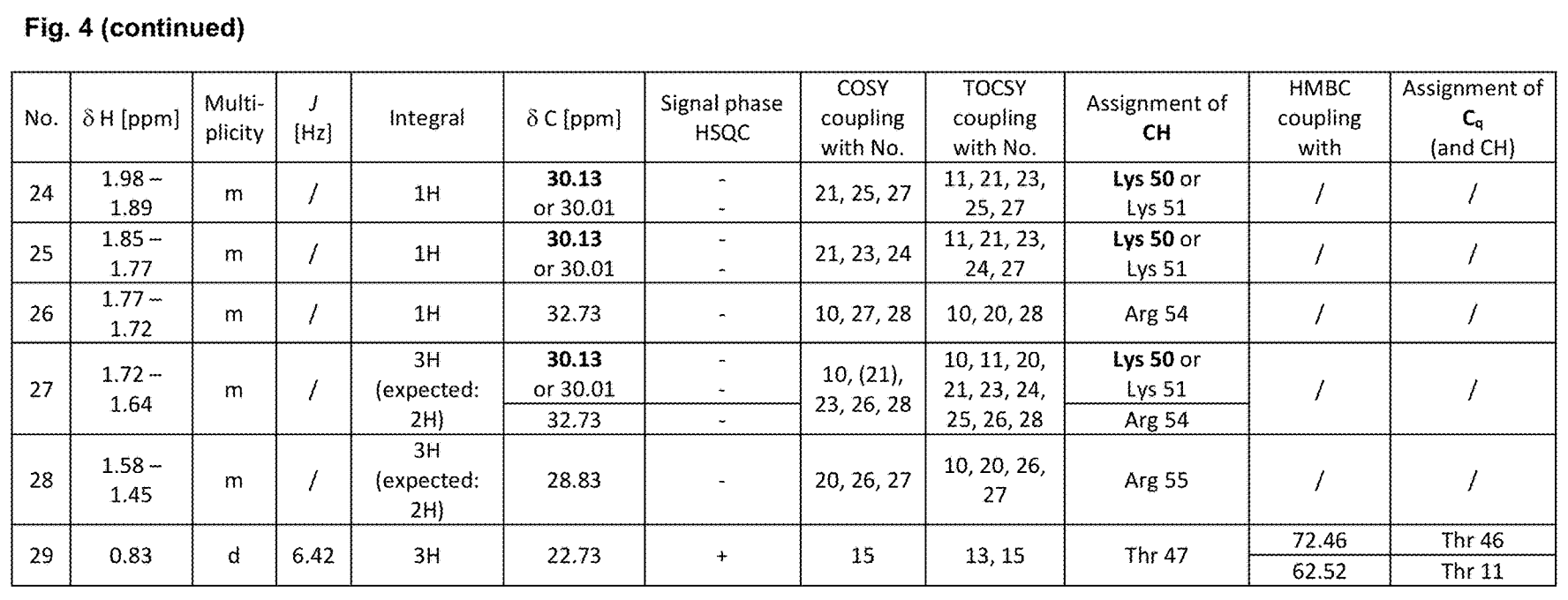

| No. | δ H [ppm] | Multi-plicity | J [Hz] | Integral | δ C [ppm] | Signal phase HSQC | COSY coupling with No. | TOCSY coupling with No. | Assignment of CH | HMBC coupling with | Assignment of Cq (and CH) |
|---|---|---|---|---|---|---|---|---|---|---|---|
| 24 | 1.98 – 1.89 | m | / | 1H | 30.13 or 30.01 | - | 21, 25, 27 | 11, 21, 23, 25, 27 | Lys 50 or Lys 51 | / | / |
| 25 | 1.85 – 1.77 | m | / | 1H | 30.13 or 30.01 | - | 21, 23, 24 | 11, 21, 23, 24, 27 | Lys 50 or Lys 51 | / | / |
| 26 | 1.77 – 1.72 | m | / | 1H | 32.73 | - | 10, 27, 28 | 10, 20, 28 | Arg 54 | / | / |
| 27 | 1.72 – 1.64 | m | / | 3H (expected: 2H) | 30.13 or 30.01 / 32.73 | - / - | 10, (21), 23, 26, 28 | 10, 11, 20, 21, 23, 24, 25, 26, 28 | Lys 50 or Lys 51 / Arg 54 | / | / |
| 28 | 1.58 – 1.45 | m | / | 3H (expected: 2H) | 28.83 | - | 20, 26, 27 | 10, 20, 26, 27 | Arg 55 | / | / |
| 29 | 0.83 | d | 6.42 | 3H | 22.73 | + | 15 | 13, 15 | Thr 47 | 72.46 / 62.52 | Thr 46 / Thr 11 |

Darobactin B $W_{49}$~$N_{50}$~$W_{51}$~$T_{52}$~$K_{53}$~$R_{54}$~$F_{55}$

Darobactin B $W_{49}$-$N_{50}$-$W_{51}$-$T_{52}$-$K_{53}$-$R_{54}$-$F_{55}$

VII

VIII

XII

XIII

XIV

XVI

XVII

XVIII darA_f/r pyrK 〉 〈 darB 〉 darC 〉 darD 〉 darE 〉 msbB

DSMko_f/r

Fig. 10C

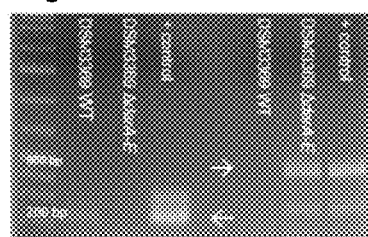

Fig. 10D

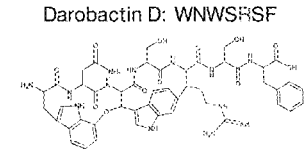

Fig. 10E

Darobactin A: WNWSKSF

Darobactin B: WNWTKRF

Darobactin B Producing Organism
*Photorhabdus asymbiotica*
*Photorhabdus australis*

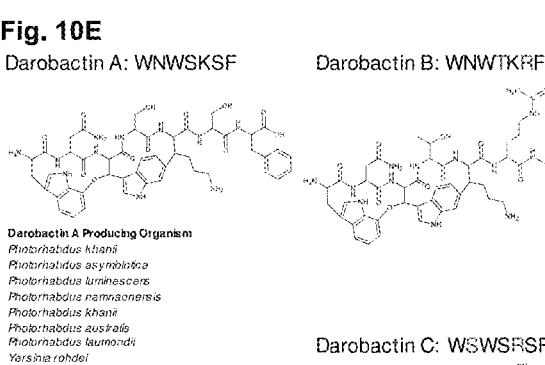

Darobactin A Producing Organism
*Photorhabdus khanii*
*Photorhabdus asymbiotica*
*Photorhabdus luminescens*
*Photorhabdus namnaonensis*
*Photorhabdus khanii*
*Photorhabdus australis*
*Photorhabdus laumondii*
*Yersinia rohdei*
*Yersinia frederiksenii*
*Yersinia massiliensis*
*Yersinia enterocolitica*
*Yersinia kristensenii*
*Yersinia intermedia*
*Yersinia aldovae*
*Vibrio crassostreae*
*Pseudoalteromonas luteoviolacea*

Darobactin C: WSWSRSF

Darobactin C Producing Organism
*Yersinia pseudotuberculosis*
*Yersinia pestis*

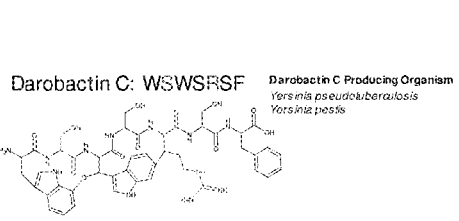

Darobactin D: WNWSRSF

Darobactin D Producing Organism
*Yersinia pseudotuberculosis*
*Yersinia enterocolitica*
*Yersinia frederiksenii*
*Yersinia aldovae*
*Yersinia pekkanenii*
*Yersinia intermedia*
*Yersinia similis*

Darobactin E: WSWSKSF

Darobactin E Producing Organism
*Yersinia bercovieri*

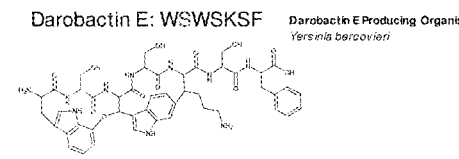

Fig. 10F

| Producing Strain | Putative Product | Propeptide Sequence |
|---|---|---|
| Photorhabdus khanii (HGB 1456) | Darobactin A | MHNTSIINCTTQEALNSLAASFKDTELSITERALDELNNKPKIPEITAWNWSKSFQEI* |
| Photorhabdus asymbiotica ATCC43949 | Darobactin B | MQNIPIETCKDQELLNSLVTSFKGTELSITEKALDELANNTEIPEINAWNWTKRFPI* |
| Photorhabdus australis strain PB68.1 | Darobactin B | MQNIPIETCKDQELLNSLVTSFKGTELSITEKALDELANNTEIPEINAWNWTKRFPI* |
| Yersinia pestis Angola | Darobactin C | MNPSSQSTVEKSNVNLIKLKSKLKSLEESFKNNPLYITSNEIDEIKNNTLHSKITAWSWSRSFAED* |
| Yersinia pseudotuberculosis strain NCTC8580 | Darobactin C | MENDMNPSSQSTVEKSNVNLIKLKSKLKSLEESFKNNPLYITSNEIDEIKNNTLHSKITAWSWSRSFAED* |
| Yersinia enterocolitica subsp. enterocolitica strain NCTC13629 | Darobactin D | MYTSHQSDLNTNNGKLIALKTKLEALDESFENNSLHISYDEIEKIKNNSLKSKITAWNWSRSFAEE* |
| Yersinia bercovieri strain SCPM-O-B-7607 | Darobactin E | MYTSHHTDRKTSNSNLMALKAKLESLDQSEKSNLLSISDHEIENLKNNNENNEITAWSWSKSFTQQ* |

Fig. 11

IXX

XX

XXI

Fig. 12

XXII

SEQUENCE LISTING

```
<160> NUMBER OF SEQ ID NOS: 49

<210> SEQ ID NO 1
<211> LENGTH: 50
<212> TYPE: DNA
<213> ORGANISM: Artificial Sequence
<220> FEATURE:
<223> OTHER INFORMATION: Primer

<400> SEQUENCE: 1
tttgacgttg gagtccacgt gttatggacg tggcaaacgc ggttcttgac            50

<210> SEQ ID NO 2
<211> LENGTH: 50
<212> TYPE: DNA
<213> ORGANISM: Artificial Sequence
<220> FEATURE:
<223> OTHER INFORMATION: Primer

<400> SEQUENCE: 2
ttgaaatatc aggatagcat tgcgctcgct caccccggtc acatagttcg            50

<210> SEQ ID NO 3
<211> LENGTH: 50
<212> TYPE: DNA
<213> ORGANISM: Artificial Sequence
<220> FEATURE:
<223> OTHER INFORMATION: Primer
```

-continued

```
<400> SEQUENCE: 3
atgctatcct gatatttcaa atgcaagtaa aatgtttcat cataataacc          50

<210> SEQ ID NO 4
<211> LENGTH: 50
<212> TYPE: DNA
<213> ORGANISM: Artificial Sequence
<220> FEATURE:
<223> OTHER INFORMATION: Primer

<400> SEQUENCE: 4
ttcttgacga gttcttctga gatgggttga tatccactga tataaatctc          50

<210> SEQ ID NO 5
<211> LENGTH: 55
<212> TYPE: DNA
<213> ORGANISM: Artificial Sequence
<220> FEATURE:
<223> OTHER INFORMATION: Primer

<400> SEQUENCE: 5
tcgagctcta aggaggttat aaaaaatgaa catcaaaaag tttgcaaaac aagca      55

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
acgtggactc caacgtcaaa                                            20

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
actcttcctt tttcaatatt attgaagcat                                30

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
tgcatttttt ataacctcct tagagctcga attcc                          35

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
tcagaagaac tcgtcaagaa ggcga                                      25

<210> SEQ ID NO 10
<211> LENGTH: 50
```

-continued

```
<212> TYPE: DNA
<213> ORGANISM: Artificial Sequence
<220> FEATURE:
<223> OTHER INFORMATION: Primer

<400> SEQUENCE: 10
tcaataatat tgaaaaagga agagtatgat tgaacaagat ggattgcacg          50

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
atctccatca aagcgctacc                                          20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ccgcgctgca actcgaaatc                                          20

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
ggtcgacgga tccccggaat agcggaaatg gcttacgaac                    40

<210> SEQ ID NO 14
<211> LENGTH: 48
<212> TYPE: DNA
<213> ORGANISM: Artificial Sequence
<220> FEATURE:
<223> OTHER INFORMATION: Primer

<400> SEQUENCE: 14
ctctaaggag gttataaaaa gcggccgcat cccttaacgt gagtttc           48

<210> SEQ ID NO 15
<211> LENGTH: 43
<212> TYPE: DNA
<213> ORGANISM: Artificial Sequence
<220> FEATURE:
<223> OTHER INFORMATION: Primer

<400> SEQUENCE: 15
aagcagctcc agcctacatc agaagaactc gtcaagaagg cga               43

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
```

-continued tttttataac ctccttagag ctcgaattcc                                                30

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
attccgggga tccgtcgacc                                                            20

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
tgtaggctgg agctgctt                                                              18

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tcccttaacg tgagttttcg                                                            20

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
ttttataacc tccttagagc tcgaa                                                      25

<210> SEQ ID NO 21
<211> LENGTH: 50
<212> TYPE: DNA
<213> ORGANISM: Artificial Sequence
<220> FEATURE:
<223> OTHER INFORMATION: Primer

<400> SEQUENCE: 21
gctctaagga ggttataaaa atgcataata ccttaaatga aaccgttaaa                           50

<210> SEQ ID NO 22
<211> LENGTH: 46
<212> TYPE: DNA
<213> ORGANISM: Artificial Sequence
<220> FEATURE:
<223> OTHER INFORMATION: Primer

<400> SEQUENCE: 22
aatagcattc atttatggct ctccttttaa atttcctgga agcttt                              46

<210> SEQ ID NO 23
<211> LENGTH: 46
<212> TYPE: DNA
<213> ORGANISM: Artificial Sequence
<220> FEATURE:
<223> OTHER INFORMATION: Primer

<400> SEQUENCE: 23
aaagcttcca ggaaatttaa aaggagagcc ataaatgaat gctatt                              46

<210> SEQ ID NO 24
<211> LENGTH: 45
<212> TYPE: DNA
<213> ORGANISM: Artificial Sequence
<220> FEATURE:
<223> OTHER INFORMATION: Primer

<400> SEQUENCE: 24
cgaaaactca cgttaaggga ttacgccgcg atggtttgtt ttatt                              45

<210> SEQ ID NO 25
<211> LENGTH: 1290
<212> TYPE: DNA
<213> ORGANISM: Photorhabdus Namnaonesis

<400> SEQUENCE: 25
atggacacca tcatcccgat caaatacctg aacgctgacg aatcttctat cctgaaaaaa           60
tctccgaaaa tcaactaccg tcagctggct tgccgtatca tcggtgaaat cccggctgaa          120
aaaatcctgg acgacgacga actggctctg tacaacgaag aaatcggtat ccacttctct          180
ccggaaatca tcaacgctaa caaactggtt gttgttgtta aagctacccg tctgtgcaac          240
ctgcgttgca cctactgcca ctcttgggct gaaggtaaag gtaacacccct gaccttcttc          300 aacctgatgc gttctatcca ccgtttcctg tctatcccga acatcaaacg tttcgaattc          360
gtttggcacg gtggtgaagt taccctgctg tctgttaact acttcaaaaa actgatctgg          420
ctgcaggaac agttcaaaaa accggaccag gttatcacca actctgttca gaccaacgct          480
gttaacatcc cggaagactg gctggttttc ctgaaaggta tcggtatggg tgttggtatc          540
tctgttgacg gtatcccgga aatccacgac tctcgtcgtc tggactaccg tggtcgtccg          600
acctctcaca agttgctgc tggtatgaaa aaactgcgtt cttacggtat cccgtacggt          660
gctctggttg ttgttgaccg tgacgtttac gaatctaaca tcgaaaaaat gctgtcttac          720
ttctacgaaa tcggtctgac cgacatcgaa ttcctgaaca tcgttccgga caaccgttgc          780
cagccgggtg acgacccggg tggttcttac atcacctacc acaactacat caacttcctg          840
tctaacgttt ccgtgtttg gtggaacgac taccaggaca aaatcaacat ccgtctgttc          900
cacggtttca tcgactctat caaatcttct cagaaaaaaa tctctgactg ctactgggct          960
ggtaactgct ctcaggaaat catcacccctg gaaccgaacg gtaccgtttc tgcttgcgac         1020
aaatacgttg gtgctgaagg taacaactac ggttctatca tcgacaacga cctgggtcac         1080
ctgctgatca aatctaacac caacaaaaac cacctgaaag aagaaatcga atcttacgaa         1140
aaaatgcacc agtgcaaatg gttccacctg tgcaacggtg gttgcccgca cgaccgtgtt         1200
accaaccgta aacacaaccc gaactacaac gacttctgct gcggtaccgg tggtctgctg         1260
gaaatcatca acagaccat cgctgcttaa                                             1290

<210> SEQ ID NO 26
<211> LENGTH: 177
<212> TYPE: DNA
<213> ORGANISM: Photorhabdus Namnaonesis

<400> SEQUENCE: 26

-continued

```
atgcacaaca cctctatcat caactgcacc acccaggaag ctctgaactc tctggctgct        60
tctttcaaag acaccgaact gtctatcacc gaacgtgctc tggacgaact gaacaacaaa       120
ccgaaaatcc cggaaatcac cgcttggaac tggtctaaat ctttccagga aatctaa         177

<210> SEQ ID NO 27
<211> LENGTH: 177
<212> TYPE: DNA
<213> ORGANISM: Pseudoalteromonas luteoviolacea

<400> SEQUENCE: 27
atgatcgttg aagctccgaa agaaaaagtt tctatctctg aaaaactgga cgctctgaaa        60
tcttctttct ctaaccagac cctgaacatc gctaacgttg accaggctcg tgttgactct       120
atctctgttg ctccgccgat caccgcttgg aactggtcta atctttcga aaaataa          177

<210> SEQ ID NO 28
<211> LENGTH: 1287
<212> TYPE: DNA
<213> ORGANISM: Pseudoalteromonas luteoviolacea

<400> SEQUENCE: 28
atgctgggtg acatctctgt taaagttatc gaagaaccgg ttaacccggt taaccagctg        60
gaactgaccg actaccagta ctctcgtctg gcttctcagc tgatcggtga aatcccggac       120
tctgacatgc tggacgaaga agaactggct ctgttccgtc gtgaaaaaga cgcttacttc       180
gaagctaaac cgctgaacgc ttctaaagtt gttgttgttc tgaaagctac ccgtctgtgc       240
aacctgcgtt gcacctactg ccactcttgg gctgaaggtc cgaaccagac cgttaaattc       300
gaaaacctga tctctatcgt taaacgtatc ctggctatcc cgaacgtttc tcgtgttgaa       360
ttcgtttggc acggtggtga agttaccctg ctgcgtccgg cttttcttcaa aaaactgatc      420 tggctgcagg aacagttcaa acgtaaagac cacttcatca ccaacaccat gcagtctaac       480
gctgttaaca tctctaaaga atggctgacc ttcctgcagg gtatcggtat ggctgttggt       540
atctctttcg acggtgttcc ggaaatcaac gacacccgtc gtctggacgt tcgtggtcgt       600
ccgacctctc tgaaagttgc tgaaggtatc aaacgtctgc aggaatacgg tatcccgtac       660
ggtgctctga tcgttgttga ccgtgacgtt tacaacgttt ctccggaacg tctgctgtct       720
tacctggctt ctatcgaact gaacgacatc gaattcctga acatcgttcc ggacaaccgt       780
gctcagccgg gtgacgacat cggtgacgct tacatctctt acaaagaata catcgaattc       840
ctgtctcgtg tttacaccgt ttggcacgct cagtaccgtg gtatcatcca gatccgtatg       900
ttcgaaaact tcatggacgt tctggctgac cgttctaaac agctgtctgc ttgctactgg       960
gctggtaact gctctcagga aatcatcacc atcgaaccga cggtgacgt ttctccgtgc       1020 gacaaatacg ttggtgacat cggttctatc tacggttctc tgctggactc tgacctggct      1080
accctgctgg ctgactctaa acacaaccag acctctgttc tggaagaagt tgaatctcac      1140
tctcgtatgc acgaatgcaa atggttctct atctgcaacg gtggttgccc gcacgaccgt      1200
gttatcaacg ctcgtcacgt tgaagactac gacgacaaat gctgcggtac cggtaaactg      1260
ctgaaagtta tcgaagaatc tatctaa                                          1287

<210> SEQ ID NO 29
<211> LENGTH: 1518
<212> TYPE: DNA
<213> ORGANISM: Pseudoalteromonas luteoviolacea

<400> SEQUENCE: 29
```

-continued

```
atggaatcta accaccaggt tgttatcatc ggtgctggtc cggctggtat gcagctgtct          60
tacttcctga acaaagcttc tgtttctcac gttgttctgg aacgtgctga catcccgggt         120
tctttcttcg ctacctaccc ggttcaccgt aaactgatct ctatcaacaa agttcacacc         180
ggtttcgacg acaaaaccaa aaacctgcgt tgggactgga actctctgct gaacgacgac         240
gacgacttct ctttcaaaga cttcgaccag tcttactacc cgtcttctga caaactggtt         300
gaatacatgg ctcagttcgc tacccgttac gaactgccga tccagttcaa cacccacgtt         360
gactctatca ccaaaaccaa ctctcagttc gttatctctt gccgtaacaa caaaacctac         420
aacgctaaca tcctggttga cgctaccggt atcggtgaac tgaacgttcc gaacatcgac         480
ggtgttgaac acgttatccc gtacaccgaa atgtctaacg acgtttctca gttcaaaaac         540
aaacgtatcc tgatcctggg taaaggtaac tctgctttcg aaaccgctga ctctctgatg         600
gaagtttctg ctaacaccca cgttatctct ccgaaagact tcaacttcgc ttgggtttct         660
cactacccgg tcacctgcg ttctgttaac cagggtttcc tggacacctt cttcctgaaa         720
cagcagaacg ctatcctgaa cggtaccatc gcttctatca aaccgaccga cagggtcag         780 tacctggttg acatgatctt ctctgaagac ggtgaacgtg aatctaacac ctacgaccac         840
atcgttaact gctctggttt caaatgcaac ttcgaccact actctgctga cctgaaaccg         900
gacctgtgcc tgatggacaa attcccgaaa ctgaaccacc agtggcagtc taccaacatc         960
gacaacctgt tcttctgcgg tgctaacatg cagtgcaacg actacaaaga ctcttctacc        1020
ccgttcgttc acggtatccg tcacaacgct cagaccctgg ctgaaatcct ggttaacaaa        1080
ctgcagaacc gtacctggca ggctaaacag accatcaccg ctgaaaccga cctgtacgac        1140
gctatctctg aacagatccg tcgtgctacc accatctggt tcctgttcgg taacgtttac        1200
gacgtttacg ctctggacgc tcagaacaac ttccagttct acgaatctat cccgaaactg        1260
gtttctgaac aggaagaact gttcaaaaac ttctctggtt acaccctgga attctcttac        1320
aaactgccga aagacgaaaa cgaaaaaccg aaattctcta cccacggttt cctgcacccg        1380
atcatcatga ataccagggg tggtgaatgc atcgacgaaa tccacatgct ggaagacatc        1440
tactctgaat gggaagacct ggacaaactg gacaacggta tcaaagaatt catcctgacc        1500
tctcagttcg aaatctaa                                                      1518
```

<210> SEQ ID NO 30
<211> LENGTH: 1065
<212> TYPE: DNA
<213> ORGANISM: Pseudoalteromonas luteoviolacea

<400> SEQUENCE: 30

```
atgaacaccc tgaccaacga actgccgaaa tgcctggaat tcaactctga caacttcgct          60
gacatcttct ctcagtgcaa aatcgacctg ctggttgaca tcttcaaacg tgaaatcctg         120
tctcacaaag aactgtctga actgttcgac aaactgtcta caccttctc ttctgaagaa         180 ctgtaccact tcttcaaact gccgaaactg tggaaagtta tcttcacctc tcgtggtaaa         240
gacaactaca tcgacaacat caaagctctg ttcctgaacg aactgaaagt tgctgaactg         300
gacaaccacg ctatctctaa ctctgctctg atcgaacagc cgcagctgat ctggaacctg         360
cgttctgaca tcgcttacaa cccgctgacc cagaaagctt acaaaaacaa ctaccagcac         420
aaagaaaccg gtatcatcat cgactacttc tctgacctgg ctcgtggtga acagcgtgac         480
atcccgtggg gtgacaccgg tatctctcag tgcctgatcg acaacaccgc tccgaaagtt         540
```

-continued

```
acctctgcta tcgactacat ccagtctgtt tctccggctt gcttcaacgt tctgaaagct        600
tctatctact ctatcgttgt tcgtttcgac accaccaaaa acatcttcaa ctgcgcttct        660
accaacatct gcaacggtct ggttgttctg atcaacccgc acctgaacga agtttctgtt        720
gaaaccctgg ctgacgctat cgttcacgaa atgaccacca acctgttcga catcgctgaa        780
ctgtacgaac cgtgcctgcc gaccaaattc cacccgcaga ccatcaaatc tccgtggacc        840
ggtcgtatgc tggacccgaa cacctacatc caggcttgct acacctggta cggtctgcgt        900
aacttctggc agaaagctta caaacacttc aacaccgaaa cgctcacaa atacctgcag        960 caggcttcta aaggtttcga acaggctgaa ttcgttcgta tcgctaaaaa ctctgacgaa       1020
atcatcaaca ccaaactgat caccaccctg gaacgtctga ataa                       1065
```

<210> SEQ ID NO 31
<211> LENGTH: 58
<212> TYPE: PRT
<213> ORGANISM: Photorhabdus Temperata

<400> SEQUENCE: 31

```
Met His Asn Thr Ser Ile Ile Asn Cys Thr Thr Gln Glu Ala Leu Asn
1               5                   10                  15

Ser Leu Ala Ala Ser Phe Lys Asp Thr Glu Leu Ser Ile Thr Glu Arg
            20                  25                  30

Ala Leu Asp Glu Leu Asn Asn Lys Pro Lys Ile Pro Glu Ile Thr Ala
        35                  40                  45

Trp Asn Trp Ser Lys Ser Phe Gln Glu Ile
    50                  55
```

<210> SEQ ID NO 32
<211> LENGTH: 58
<212> TYPE: PRT
<213> ORGANISM: Photorhabdus khanii

<400> SEQUENCE: 32

```
Met His Asn Thr Leu Asn Glu Thr Val Lys Thr Gln Glu Ala Leu Asn
1               5                   10                  15

Ser Leu Ala Ala Ser Phe Lys Glu Thr Glu Leu Ser Ile Thr Asp Lys
            20                  25                  30

Ala Leu Asn Glu Leu Ser Asn Lys Pro Lys Ile Pro Glu Ile Thr Ala
        35                  40                  45

Trp Asn Trp Ser Lys Ser Phe Gln Glu Ile
    50                  55
```

<210> SEQ ID NO 33
<211> LENGTH: 58
<212> TYPE: PRT
<213> ORGANISM: Photorhabdus australis

<400> SEQUENCE: 33

```
Met Gln Asn Thr Leu Val Glu Thr Cys Lys Thr Gln Glu Ala Leu Asn
1               5                   10                  15

Ser Leu Ala Ala Ser Phe Lys Glu Thr Glu Leu Ser Ile Thr Glu Lys
            20                  25                  30

Ala Leu Asn Glu Leu Ser Ser Lys Pro Lys Ile Pro Glu Ile Thr Ala
        35                  40                  45

Trp Asn Trp Ser Lys Ser Phe Gln Glu Ile
    50                  55
```

```
<210> SEQ ID NO 34
<211> LENGTH: 58
<212> TYPE: PRT
<213> ORGANISM: Photorhabdus laumondii

<400> SEQUENCE: 34

Met His Asn Thr Ser Ile Ile Asn Cys Thr Thr Gln Glu Ala Leu Asn
1               5                   10                  15

Ser Leu Ala Ala Ser Phe Lys Asp Thr Glu Leu Ser Ile Thr Glu Arg
            20                  25                  30

Ala Leu Asp Glu Leu Asn Asn Lys Pro Lys Ile Pro Glu Ile Thr Ala
        35                  40                  45

Trp Asn Trp Ser Lys Ser Phe Gln Glu Ile
        50                  55

<210> SEQ ID NO 35
<211> LENGTH: 66
<212> TYPE: PRT
<213> ORGANISM: Yersinia frederiksenii

<400> SEQUENCE: 35

Met His Thr Ser His Gln Pro Asp Lys Lys Thr Gly Asn Thr His Leu
1               5                   10                  15

Ile Thr Leu Lys Thr Lys Leu Glu Ser Leu Glu Glu Ser Phe Lys Asn
            20                  25                  30

Ser Ser Leu Ser Ile Asn Asp His Glu Ile Glu Ser Leu Lys Asn Ser
        35                  40                  45

Asp Ser Asp Asn Lys Ile Thr Ala Trp Asn Trp Ser Lys Ser Phe Thr
    50                  55                  60

Gln Gln
65

<210> SEQ ID NO 36
<211> LENGTH: 55
<212> TYPE: PRT
<213> ORGANISM: Vibrio tasmaniensis

<400> SEQUENCE: 36

Met Ile Ile Val Glu Lys Glu Lys Val Ser Ile Ser Glu Arg Leu Asp
1               5                   10                  15

Ala Leu Met Ser Ser Phe Ser Glu Met Asn Leu Glu Leu Thr Lys Phe
            20                  25                  30

Asp Gln Glu Gln Val Asn Ser Ile Asn Ile Ala Pro Pro Ile Thr Ala
        35                  40                  45

Trp Asn Trp Ser Lys Ser Phe
    50                  55

<210> SEQ ID NO 37
<211> LENGTH: 58
<212> TYPE: PRT
<213> ORGANISM: Pseudoalteromonas luteoviolacea

<400> SEQUENCE: 37

Met Ile Val Glu Ala Pro Lys Glu Lys Val Ser Ile Ser Glu Lys Leu
1               5                   10                  15

Asp Ala Leu Lys Ser Ser Phe Ser Asn Gln Thr Leu Asn Ile Ala Asn
            20                  25                  30

Val Asp Gln Ala Arg Val Asp Ser Ile Ser Val Ala Pro Pro Ile Thr
        35                  40                  45
```

-continued

```
Ala Trp Asn Trp Ser Lys Ser Phe Glu Lys
    50                  55

<210> SEQ ID NO 38
<211> LENGTH: 7
<212> TYPE: PRT
<213> ORGANISM: Photorhabdus sp.

<400> SEQUENCE: 38

Trp Asn Trp Ser Lys Ser Phe
1               5

<210> SEQ ID NO 39
<211> LENGTH: 7
<212> TYPE: PRT
<213> ORGANISM: Photorhabdus sp.

<400> SEQUENCE: 39

Trp Asn Trp Thr Lys Arg Phe
1               5

<210> SEQ ID NO 40
<211> LENGTH: 7
<212> TYPE: PRT
<213> ORGANISM: Yersinia sp.

<400> SEQUENCE: 40

Trp Ser Trp Ser Arg Ser Phe
1               5

<210> SEQ ID NO 41
<211> LENGTH: 7
<212> TYPE: PRT
<213> ORGANISM: Yersinia sp.

<400> SEQUENCE: 41

Trp Asn Trp Ser Arg Ser Phe
1               5

<210> SEQ ID NO 42
<211> LENGTH: 7
<212> TYPE: PRT
<213> ORGANISM: Yersinia bercovieri

<400> SEQUENCE: 42

Trp Ser Trp Ser Lys Ser Phe
1               5

<210> SEQ ID NO 43
<211> LENGTH: 57
<212> TYPE: PRT
<213> ORGANISM: Photorhabdus asymbiotica

<400> SEQUENCE: 43

Met Gln Asn Ile Pro Ile Glu Thr Cys Lys Asp Gln Glu Leu Leu Asn
1               5                   10                  15

Ser Leu Val Thr Ser Phe Lys Gly Thr Glu Leu Ser Ile Thr Glu Lys
            20                  25                  30

Ala Leu Asp Glu Leu Ala Asn Asn Thr Glu Ile Pro Glu Ile Asn Ala
        35                  40                  45

Trp Asn Trp Thr Lys Arg Phe Pro Ile
    50                  55
```

<210> SEQ ID NO 44
<211> LENGTH: 67
<212> TYPE: PRT
<213> ORGANISM: Yersinia pestis

<400> SEQUENCE: 44

Met Asn Pro Ser Ser Gln Ser Thr Val Glu Lys Ser Asn Val Asn Leu
1               5                   10                  15

Ile Lys Leu Lys Ser Lys Lys Leu Lys Ser Leu Glu Glu Ser Phe Lys
            20                  25                  30

Asn Asn Pro Leu Tyr Ile Thr Ser Asn Glu Ile Asp Glu Ile Lys Asn
        35                  40                  45

Asn Thr Leu His Ser Lys Ile Thr Ala Trp Ser Trp Ser Arg Ser Phe
    50                  55                  60

Ala Glu Asp
65

<210> SEQ ID NO 45
<211> LENGTH: 70
<212> TYPE: PRT
<213> ORGANISM: Yersinia pseudotuberculosis

<400> SEQUENCE: 45

Met Glu Asn Asp Met Asn Pro Ser Ser Gln Ser Thr Val Glu Lys Ser
1               5                   10                  15

Asn Val Asn Leu Ile Lys Leu Lys Ser Lys Leu Lys Ser Leu Glu Glu
            20                  25                  30

Ser Phe Lys Asn Asn Pro Leu Tyr Ile Thr Ser Asn Glu Ile Asp Glu
        35                  40                  45

Ile Lys Asn Asn Thr Leu His Ser Lys Ile Thr Ala Trp Ser Trp Ser
    50                  55                  60

Arg Ser Phe Ala Glu Asp
65                  70

<210> SEQ ID NO 46
<211> LENGTH: 66
<212> TYPE: PRT
<213> ORGANISM: Yersinia enterocolitica

<400> SEQUENCE: 46

Met Tyr Thr Ser His Gln Ser Asp Leu Asn Thr Asn Asn Gly Lys Leu
1               5                   10                  15

Ile Ala Leu Lys Thr Lys Leu Glu Ala Leu Asp Glu Ser Phe Glu Asn
            20                  25                  30

Asn Ser Leu His Ile Ser Tyr Asp Glu Ile Glu Lys Ile Lys Asn Asn
        35                  40                  45

Ser Leu Lys Ser Lys Ile Thr Ala Trp Asn Trp Ser Arg Ser Phe Ala
    50                  55                  60

Glu Glu
65

<210> SEQ ID NO 47
<211> LENGTH: 66
<212> TYPE: PRT
<213> ORGANISM: Yersinia bercovieri

<400> SEQUENCE: 47

Met Tyr Thr Ser His His Thr Asp Arg Lys Thr Ser Asn Ser Asn Leu
1               5                   10                  15

-continued

```
Met Ala Leu Lys Ala Lys Leu Glu Ser Leu Asp Gln Ser Phe Lys Ser
            20                  25                  30

Asn Leu Leu Ser Ile Ser Asp His Glu Ile Glu Asn Leu Lys Asn Asn
            35                  40                  45

Asn Phe Asn Asn Glu Ile Thr Ala Trp Ser Trp Ser Lys Ser Phe Thr
            50                  55                  60

Gln Gln
65

<210> SEQ ID NO 48
<211> LENGTH: 4
<212> TYPE: PRT
<213> ORGANISM: Artificial Sequence
<220> FEATURE:
<223> OTHER INFORMATION: Synthetic construct

<400> SEQUENCE: 48

Ser Lys Ser Phe
1

<210> SEQ ID NO 49
<211> LENGTH: 4
<212> TYPE: PRT
<213> ORGANISM: Artificial Sequence
<220> FEATURE:
<223> OTHER INFORMATION: Synthetic construct

<400> SEQUENCE: 49

Thr Lys Arg Phe
1
```

ANTIBIOTIC SELECTIVELY KILLS GRAM-NEGATIVE PATHOGENS

CROSS-REFERENCE TO RELATED APPLICATION

This application is a national phase entry under 35 USC § 371 of International Application No. PCT/EP2020/025531, filed on Nov. 20, 2020, which claims the benefit of and priority to European Patent Application No. 19210353.9, filed on Nov. 20, 2019. The entire disclosure of which are incorporated herein by reference.

INCORPORATION BY REFERENCE OF MATERIAL SUBMITTED ELECTRONICALLY

This application contains, as a separate part of disclosure, a sequence listing in computer-readable form (57806_Seq-listing.txt; Size: 16,821 Bytes; Created: May 17, 2022) which is incorporated by reference in its entirety.

The invention relates to bicyclic heptapeptide antibiotics, derivatives thereof, and their manufacturing (production) and usage as active pharmaceutical ingredients (APIs) in medicaments against Gram-negative pathogens.

Incorporation by Reference of the Sequence Listing

This application contains, as a separate part of disclosure, a Sequence Listing in computer-readable form (Filename: 57806_SubSeqListing.txt; Size: 20,764 bytes;

Created: Dec. 30, 2025) which is incorporated by reference herein in its entirety.

DESCRIPTION

Background of the Technology

The current need for novel antibiotics is especially acute for drug-resistant Gram-negative pathogens. These micro-organisms have a highly restrictive permeability barrier, which limits penetration of most compounds. As a result, the last class of antibiotics acting against Gram-negative bacteria was developed in the 60s years of the last century.

It is difficult to find compounds acting against Gram-negative bacteria. Gram-negative bacteria have an outer membrane to protect themselves from unwanted compounds. This membrane is decorated with an outer layer of negatively charged lipopolysaccharide (LPS), which serves as a barrier for large and hydrophobic compounds. The inner membrane limits the permeability by hydrophilic compounds.

As a result, the combined barrier (outer membrane plus inner membrane) restricts all molecules, and nutrients enter through outer membrane porins and specialized transporters. Drugs that leak through the barrier are extruded by trans-envelope multidrug resistance pumps (MDRs) that recognize amphiphilic compounds, which most drugs are in order to pass hydrophilic regions of cells as well as hydrophobic. regions (e. g. membranes). Thus, there is great need within the state of the art for APIs with different working-mechanisms, being unhindered by the triple-defense-line of Gram-negative bacteria (outer membrane, inner membrane and MDRs).

CONTENT OF THE INVENTION

Darobactin A (DAR) is a ribosomally synthesized and post-translationally modified. peptide (RiPP) antibiotic, which was initially identified from bacteria belonging to the genus *Photorhabdus*. In addition, the corresponding biosynthetic gene cluster (BGC) was identified and subsequently detected in several bacterial genera. DAR represents a highly promising lead structure for the development of novel antibacterial therapeutic agents. It targets the outer membrane protein BamA and is therefore specific for Gram-negative bacteria. This, together with the convincing in vivo activities in mouse infection models, makes it a particular promising candidate for further research. To improve compound supply for further investigation of DAR and to enable production of novel derivatives, establishment of an efficient and versatile microbial production platform for these class of RiPP antibiotics is highly desirable. Herein design and construction of a heterologous production and engineering platform for DAR and/or its derivatives is revealed, which will ensure production yield and facilitates structure modification approaches. The known Gram-negative workhorses *Escherichia coli* and *Vibrio natriegens* were tested as heterologous hosts. In addition to that, DAR producer strains were generated and optimization of the expression constructs yielded production titers of DAR showing around 10-fold increase in concentration (titer) and 5-fold decrease in fermentation time compared to the product descriptions according to the state of the art. Also, the identification of the minimal DAR BGC is revealed, since only two genes are necessary for heterologous production of the RiPP (Darobactin and/or its derivatives).

DAR, the novel antibiotic that selectively kills Gram-negative pathogens, e.g. *Acinetobacter baumannii* (MIC, 8 g/ml), *Pseudomonas aeruginosa* PAO1 (MIC, 2 µg/ml), *Escherichia coli* wild type and MDR strains (MIC, 2-4 µg/ml), *Klebsiella pneumoniae* (MIC, 2-4 µg/ml), and *Salmonella enteritidis* (MIC, 4 µg/ml), was discovered in *Photorhabdus khanii* HGB1456. Other natural occurring derivatives, e.g. darobactin B, as well as brominated variants resp, derivatives show activity against *E. coli* wild type and MDR strains (MIC, 0.5-1 µg/ml), *Klebsiella pneumoniae* (MIC, 1 µg/ml), and *Salmonella enteritidis* (MIC, 1 µg/ml). Experimental proof was provided that DAR binds to BamA, which is the central component of the OM B-barrel assembly machinery. It helps to fold and insert B-barrel proteins such as porins into the OM. If this chaperone-like function is impaired, it will result in the disruption of OM formation. In addition to its good in vitro activity, DAR showed promising efficacy in mouse septicemia and thigh infection models without cytotoxic effects. Therefore, DAR has emerged as a promising drug lead.

An objective of the present invention is to provide new substances that can be used as pharmaceutical active ingredients (APIs) for medicaments being effective against Gram-negative bacteria in a new and unexpected way and against which there are therefore no resistances existing among Gram-negative bacteria. Surprisingly, bicyclic heptapeptides according to formula 1 are exerting characteristics/interactions with cellular components providing these positive effects: They act against an attractive, but also highly unusual target—the BamA chaperone and translocator. The BamA chaperone and translocator helps fold and insert β-barrel proteins such as porins into the outer membrane. BamA itself is an outer membrane β-barrel protein. Drugs in general, and natural products in particular, normally target enzymes with their well-defined catalytic centers, rather than chaperones. Darobactin is a large molecule, which is probably necessary to interfere with the protein-protein binding between BamA and its substrates. The location of the target on the surface resolves the intractable problem of penetration across the permeability barrier of Gram-negative bacteria, none is necessary in the case of darobactin. There are only two essential proteins exposed on the surface of the outer membrane-BamA; and LptD. Therefore, bicyclic heptapeptides that target BamA are bypassing the triple-defense-line of Gram-negative bacteria (outer membrane, inner membrane and MDRs) effectively and offer a new mode of action for antibiotic activity.

ribosomal synthesis of darobactins suggests that the amino acid backbone is in L-configuration. The macrocycle cross linkages generate two chiral centers at the β-carbons of W3 and K5, which have R and S configurations, respectively, based on NOE correlations (FIG. 4). The putative operon coding for darobactin biosynthesis (FIGS. 2A, 2B and 2C) is typical of RiPPs that code for a variety of ribosomally-produced natural products, including the antibiotics nisin, a Scheme 1: general formula I of bicyclic heptapeptides (I)

In Scheme I the substituents and indexes have the following values: $R^1$, $R^2$, $R^3$, $R^4$ are independently from each other selected from the list comprising H, —$CH_3$, —$CH_2$—$CH_2$—$CH_2$—NH—$C(NH)(NH_2)$, —$CH_2$—CO—$NH_2$, —$CH_2$—$CO_2H$, —$CH_2$—SH, —$CH_2$—$CH_2$—$CO_2H$, —$CH_2$—$CH_2$—CO—$NH_2$, (1H-imidazole-4-yl)-methyl, halogenated (1H-imidazole-4-yl)-methyl, —$CH(CH_3)$ $(C_2H_5)$, —$CH_2$—$CH(CH_3)_2$, —$CH_2$—$CH_2$—$CH_2$—$CH_2NH_3$, —$CH_2$—$CH_2$—S—$CH_3$, —$CH_2$—$C_6H_5$, halogenated-$CH_2$—$C_6H_5$, (1H-indol-3-yl)-methyl, halogenated (1H-indol-3-yl)-methyl, (4-hydroxyphenyl)-methyl, halogenated (4-hydroxyphenyl)-methyl, —CH—$(CH_3)_2$, 1-hydroxy-ethyl, hydroxy-methyl, sec-butyl, 1-acetamide, 1-thioacetamide, —$CH_2$—$CH_2$—NH—$(C{=}NH)$—$NH_2$, benzyl, halogenated benzyl, —$CH_2$—$CH_2$—$CH_2$—NH— $(C{=}NH)$—$NH_2$. X is at any position of X independently from any other position of X either O or S. $R^5$ is selected from the list comprising methylsulfonyl, p-toluenesulfonyl; $R^6$ is selected from the list comprising methylsulfonyl, p-toluenesulfonyl, —$(C{=}NH)$—$NH_2$. $Z^1$, $Z^2$ each are a double bond or a single bond in such a way that $Z^1$ and $Z^2$ both are single bonds or only one of them is a single bond and the other one is a double bond at the same time whereat $Z^1$ is the single bond and $Z^2$ is the double bond or vice versa. $Y^1$ is 3,7-indolylene or halogenated 3,7-indolylene and $Y^2$ is independently selected from the list 3,6-indolylene, 1,4-phenoxylene, halogenated 3,6-indolylene, halogenated 1,4-phenoxylene and n is 1 or 2.

Darobactin is a modified heptapeptide with an amino acid sequence $W^1$—$N^2$—$W^3$-$S^4$-$K^5$—$S^6$—$F^7$ (SEQ ID NO: 38). NMR studies revealed two unusual macrocycle cross linkages in darobactin: an unprecedented aromatic-aliphatic ether linkage between the C7 indole of $W^1$ and the β-carbon of $W^3$, and a carbon-carbon bond between the C6 indole of $W^3$ and the β-carbon of $K^5$. The tryptophan-lysine bond is made between two unactivated carbons, which is unique for an antibiotic. This bicyclic structure is characteristic and essential for darobactin A and all inventive derivatives.

Directly comparing the sequence of this 7 amino acid peptide (darobactin A) against the genome of *P. temperata* reveals a perfect match near the C-terminus of an open reading frame coding for a 58 amino acid long peptide. The food preservative and thiostrepton. This dar operon consists of the propeptide encoded by darA, a small relE-type ORF which may play a role in host resistance to the compound, darBCD coding for an ABC-type transenvelope exporter, and darE for a radical SAM enzyme. The radical SAM class of enzymes catalyze free radical-based reactions that can link unactivated carbons. This would explain the formation of the tryptophan-lysine C—C bond in darobactin and its derivatives. Such a Trp-Lys C—C bond was recently reported in a peptide pheromone, streptide, from *Streptococcus thermophilus*. There is little overall homology between the two enzymes, but DarE contains the SAM and SPASM domains characteristic for this group. The operon does not contain a separate enzyme for making the ether bond in the first ring. RiPP operons often code for a protease that cleaves out the active peptide; this was not present in the dar operon. Hence, generic proteolysis, self-cleavage or other proteases present in producer strains can be involved in maturation of the propeptide. Surprisingly, it appears that the DarE radical SAM enzyme catalyzes the formation of both the Trp-Lys C—C bond, and the C—O—C Trp-Trp ether bond. The chemistries of these two reactions are quite different, and the mechanism of DarE catalysis clearly requires a separate investigation. To link the putative BGC with darobactin production, we generated a markerless knockout mutant in which the complete BGC darABCDE was deleted from *Photorhabdus* khanii DSM3369 by double crossover. DAR production was abolished in the resulting mutant strain; no molecule with a corresponding molecular weight could be detected by MS (FIG. 10D). Importantly, darobactin was produced heterologously from the dar operon cloned into *E. coli* (FIGS. 10A and 10B). This shows that the dar operon is sufficient for making darobactin. We find that the dar operon is common in *Photorhabdus*, and we detected it in 16 different species for which the genome sequence is available (FIG. 2*a*; FIG. 10E). The dar operon was only absent in *P. bodei*. Synteny of the genomes containing the dar locus with that of *P. bodei* helped determine the boundaries of the operon (FIG. 2*a*). We also tested production of darobactin in several different *Photorhabdus*, and found that it is the highest in a strain of *P. khanii* DSM 3369, from the Deutsche Sammlung von Mikroorganismen und Zellkulturen (DSMZ) culture collection. This shows that strains harboring the BGC are producing the compound.

We then expanded the search for dar-type operons in databases of bacterial genome sequences (NCBI), using the propeptide and the dar encoding peptide as queries. The two searches identified homologues of the dar operon that appear to code for four darobactin analogs. We therefore propose the name darobactin A for the first compound, and darobactin B-E for the predicted analogs of this class of antibiotics. In *Photorhabdus australis* and *Photorhabdus asymbiotica*, the sequence data suggest production of darobactin B, which contains two amino acid changes on the N-terminus (SKSF (SEQ ID NO: 48)→TKRF (SEQ ID NO: 49). In multiple *Yersinia* species either the second amino acid (N→S) or the fifth amino acid (K→R), or both, are modified. We named these analogs darobactin C, D, and E. Interestingly, darobactin C sequence is present in *Yersinia pestis*, the causative agent of plague, and by (resp. in) *Y. frederiksenii* from the human gut microbiome. The putative structures of darobactin B-E deduced from the amino acid sequence are shown in FIG. 10F. Among the five compounds, darobactin A is the most common, and a corresponding propeptide sequence is present in 9 sequenced *Photorhabdus* species, 7 *Yersinia* species, *Vibrio crassostreae*, and *Pseudoalteromonas luteoviolacea*, all of which are y-proteobacteria. Additional members of this class of antibiotics are likely to emerge as more bacterial genomes 'are sequenced.

These experiments suggest that darobactin is a promising lead compound for developing a therapeutic or a medical preparation against Gram-negative pathogens. The experimental results presented herein show that bicyclic heptapeptides derived from DAR are effective compounds (APIs) for medical preparations against Gram-negative pathogens. A medical preparation comprising darobactin and/or bicyclic heptapeptides is effective in vertebrates like birds, fishes, amphibians, reptiles and mammals and human suffering from an infection caused by Gram-negative bacteria. The Gram-negative bacteria are selected from the group *Pseudomonas aeruginosa, Klebsiella pneumoniae, Acinetobacter baumannii, Neisseria gonorrhoeae, Chlamydia trachomatis, Shigella sonnei, Salmonella enterica Typhimurium LT2, Enterobacter cloacae, Bifidobacterium longum, Bacteroides fragilis, Lactobacillus reuteri, Enterococcus faecalis* and *Yersinia pestis*. This group is not meant to be restricting the scope of the invention—there are many other Gram-negative bacteria also belonging to this group, for example *Pseudomonas, fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Enterobacter aerogenes, Enterobacter* spp., *Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria mono-*

*cytogenes, Neisseria meningitidis, Kingella, Moraxella, Gardnerella vaginalis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides* splanchnicus.

For manufacturing/production of bicyclic heptapeptides and derivatives we choose several different heterologous hosts, cloned the respective DAR BGC from different species, including upstream regions of the BGC, and lastly created a DAR-resistant heterologous host to boost DAR production.

Detailed Embodiments of the Invention

The following embodiments of the invention are examples of preferred embodiments which are nevertheless not meant to be confining the scope of the invention. It is obvious to the person skilled in the art, that similar microbial strains to the ones revealed herein can also be used without leaving the scope of the invention. The same is true for the chemical modifications revealed herein below, the steps of the manufacturing process and the presented pharmaceutical formulations and ways of application.

General Description of Fermentation of *Photorhabdus* Spp, for Production of Bicyclic Heptapeptides:

*Photorhabdus* sp. strains are inoculated in a suitable growth medium (e.g. 3 mL lysogeny broth: 10 g tryptone, 5 g yeast extract, 5 g NaCl) and incubated to promote growth. An aliquot of this pre-culture is used to inoculate the main culture (e.g. LB medium in shaking flasks and incubated to promote growth until harvesting.

General Description of Fermentation of *Pseudoalteromonas* Strains for Production of Bicyclic Heptapeptides:

*Pseudoalteromonas* strains such as *Pseudoalteromonas luteoviolacea* $H_{33}$ and H33S containing the biosynthetic gene cluster corresponding to the expression of bicyclic heptapeptides (e.g., composed of 8 genes coding for the propeptide, the modifying radical SAM enzyme, an FAD-dependent halogenase, one gene of unknown function and four transporter genes), are cultivated in suited medium, such as Marine Broth or similar medium containing a buffered artificial seawater formulation, a suited carbon source, e.g. sugars (such as glucose, rhamnose), a suited nitrogen source, e.g. ammonium containing salts (such as $NH_4Cl$) or a complex carbon and nitrogen source, e.g. casitone or yeast extract. Cultures are incubated at a suited temperature (4° C.-40° C.) in volumes from 20 mL to 2 L with or without shaking (or in a production-scale fermenter with or without stirring/mixing) and with or without addition of small molecule inducers such as N-acyl-homoserinelactone derivatives for 1 to 7 days. Culture medium is separated from the cells, e.g. by centrifugation, and cleared medium is further processed for purification. From strains carrying the BGC with an FAD-dependent halogenase and one gene of unknown function in addition to the *Photorhabdus* BGC, halogenated (e.g. Cl, Br, I, F) and non-halogenated bicyclic heptapeptides and variants either carrying or not carrying an additional double bond (e.g. dehydro-derivatives) can be isolated. For the generation of halogenated derivatives, suitable enzymes, as the FAD-dependent halogenase encoded in the BGCs of *Pseudoalteromonas luteoviolacea* H33 and H33S, can be used in vivo or in vitro. As it is known to the person skilled in the art, the position of the halogen within the aromatic ring can be altered by the usage of different halogenases, which are catalyzing halogenation at a specific position.

It is also well known within the state of the art that there are also naturally existing polyhalogenated (e. g. polybrominated, polychlorinated) compounds, e.g. produced by marine organisms. Therefore, the scope of the invention obviously also comprises polyhalogenated bicyclic heptapeptides. Scheme 1 shows the aromatic and heteroaromatic sub-structures of the bicyclic heptapeptides which are possibly mono- or poly-halogenated.

IIa

IIb

IIc

IId

IIe

IIf

Scheme 2: possible halogenated sub-structures IIa-IIf of bicyclic heptapeptides according to formula I whereat substituents $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$ are independently from each other H, F, Cl, Br, I.

Sub-structure IIa is describing halogenated 3,7-indolylene as $Y^1$ in formula I, sub-structure IIb is describing halogenated 3,6-indolylene as $Y^2$ in formula I, sub-structure IIc is describing halogenated 1,4-phenoxylene as $Y^2$ in formula I and sub-structures IId, IIe, IIf as well as sub-structure IIc are describing any halogenated aromatic or heteroaromatic substituent $R^1$, $R^2$, $R^3$, $R^4$ in formula I, especially: halogenated (1H-imidazole-4-yl)-methyl, halogenated-$CH_2$—$C_6H_5$, halogenated (1H-indol-3-yl)-methyl, halogenated (4-hydroxyphenyl)-methyl, halogenated benzyl.

Preparations containing the FAD-dependent halogenase can be used for halogenation of bicyclic heptapeptides. Enzyme can be heterologously overexpressed and purified by procedures well known by the person skilled in the art. Purified enzyme (100 μL) was incubated with 10 μL purified Flavin reductase (Enzyme can be generated by procedures well known by the person skilled in the art), 10 μM FAD, 2.4 mM NADH, 25 mM KBr, 0.15 mM Substrate (e.g. darobactin A) and 10 mM potassium phosphate buffer (pH 7.2) in a total volume of 300 μL. The reaction was incubated 24 h at 18° C. and stopped by adding an equal amount of methanol bevor LC-MS analysis. The resulting product was brominated darobactin A.

General Methods for Purification of Bicyclic Heptapeptides:

Method A:

Cells are pelleted by centrifugation at 10,000×g for 5 minutes and the supernatant is collected in a round bottom flask for lyophilization. The dried supernatant is washed twice with methanol. After the second washing step, the methanol is removed completely and deionized water is added to dissolve the crude extract. Centrifugation step at 10,000×g for 5 minutes is done to remove insoluble part. Then, the crude extract is subjected to reverse phase flash chromatography (Interchim Puriflash 4125 chromatography system equipped with a Puriflash C18—HP30 mm Flash column, gradient elution of 5% MeOH/$H_2O$ to 100% MeOH over 1 h). The fraction containing DAR is further purified by HPLC. A C18 column (Macherey Nagel, EC 250/4.6 Nucleodur C18 Gravity-SB, 5 μm) is used, with the following method:

| Time (min) | Methanol (Solvent B) |
| --- | --- |
| 0-20 | 25%-45% |
| 20-22 | 45% |
| 22.10-30 | 100% |
| 30.10-38 | 25% |

Solvent A is 0.1% trifluoroacetic acid in water. The solvents are pumped through the HPLC system with the flowrate of 1 mL/min. DAR is collected by fraction collector from 15.90-17.10 minutes.

Method B:

Cleared medium is applied to a hydrophobic interaction material (e.g. C18 silica, Amberlite XAD-16N), washed with $H_2O$ and eluted with a mixture of organic solvent (e.g. MeOH, MeCN) and $H_2O$ with or without 0.1% formic acid. Eluate is concentrated and organic solvent is removed in vacuo and the now aqueous elution is loaded to a strong cation ion exchange material (e.g. SP Sepharose XL).

Subsequently, this material is washed with 0.1% formic acid and the material bound to the column is eluted using a suited buffer system such as $NH_4CH_3COO$ with pH 5 to pH 11. Fractions are analysed by LCMS and fractions containing the compound of interest are pooled, bound to a hydrophobic interaction material (e.g. C18 silica, Amberlite XAD-16N) and eluted in a gradient with $H_2O$ and an organic solvent (e.g. MeCN). Peaks are collected based on UV absorption and collected fractions are analysed by LCMS. Peptides of interest containing fractions are separated by HPLC with a gradient of $H_2O$ and a suited organic solvent (e.g. MeOH, MeCN). Peaks are collected to yield the pure compounds of interest.

It is well known to the person skilled in the art that peptides of any type being produced by fermentation processes as described above can additionally be chemically modified, e.g. by reacting them with different equivalents of Lawson's Reagent, O,O-diethyl ammonium phosphorodithioate salt, $P_4S_{10}$/dimethicone, $PSCl_3/H_2O/Et_3N$, or other reagents, optionally supported by a suitable protection group strategy. By doing so it is possible to acquire substitution of one or even all amide bonds by thioamide-bonds. Furthermore, conversion of amino groups to sulfonamides is possible by treatment (of the optionally protected substrates) with mesyl chloride, tosyl chloride or other suitable reagents. Bicyclic heptapeptides chemically modified in this or in other ways are therefore also comprised by the scope of the invention.

Heterologous Darobactin A Expression and Identification of the Minimal Biosynthetic Gene Cluster The scope of the invention comprises the generation of expression constructs, applying e.g. different promoters, ribosomal binding sites, and further elements for regulation of expression, by transferring the genes needed for the biosynthesis into any state of the art expression vector, as is obvious to the person skilled in the art. Therefore, the following example is not meant to be confining the scope of the invention.

Exemplarily several constructs were generated during this project for heterologous expression of DAR (FIG. 3). In this example, the vector background used for the expression constructs was pRSFDuet™-1 (Merck KGaA, Darmstadt, Germany). Chromosomal DNA used as template for amplification of the DAR BGC was isolated using the innuPREP Bacteria DNA Kit (Analytik Jena AG, Jena, Germany). In general, fragments were amplified using Q5 DNA polymerase (New England Biolabs, Ipswich, USA) and purified from the agarose gel using Large Fragment DNA Recovery Kit (Zymo Research, Irvine, USA). The polymerase chain reaction (PCR) was performed in a Biometra TRIO thermocycler (Analytik Jena AG, Jena, Germany) using the following program: 95° C. for 2 minutes; 34 cycles of 95° C. for 45 seconds, 60-70° C. for 45 seconds (applied annealing temperature was depending on the primer sequence), 72° C. for 30 seconds/kb (extension time was varied depending on the length of the fragment to be amplified), followed by a final extension step at 72° C. for 5 minutes.

It is obvious to the person skilled in the art that the scope of the invention comprises the use of any organism carrying the biosynthetic gene cluster (BGC) and amplifying or synthesizing a native or codon-optimized version of the BGC (parts or complete) and cloning it into an expression vector. The vector is then transferred into an expression host. Therefore, the following example is not meant to be confining the scope of the invention.

SEQ ID NO: 25 shows codon-optimized darE from *Photorhabdus*_namnaonensis. SEQ ID NO: 26 shows codon-optimized darA from *Photorhabdus*_namnaonensis. SEQ ID NO: 27 shows codon-optimized darA from *Pseudoalteromonas*_luteoviolacea. SEQ ID NO: 28 shows codon-optimized darE from Pseudoalteromonas_luteoviolacea. SEQ ID NO: 29 shows Pseudoalteromonas_luteoviolacea_Darobactin-halogenase_codon-optimized. SEQ ID NO: 30 shows Pseudoalteromonas_luteoviolacea_protein_wo_homology_codon-optimized.

Plasmid pZW-ADC3 carries the genes of the DAR BGC without the intergenic region between darA and darB. Therefore, darA was amplified from *Photorhabdus khanii* HGB1456 using a primer pair; and darB to darE was amplified using respective primers, all these amplifications being performed according to methods as are known to the person skilled in the art. pRSFDuet™-1 was linearized using NdeI and AvrII restriction enzymes (New England Biolabs, Ipswich, USA) to insert the two purified fragments into the second multiple cloning site of the vector under the control of the T7/ac promoter. To do this, the one-step isothermal DNA assembly protocol described by Gibson was followed, with the minor modification that 1.2 µl of 10 U/µL T5 exonuclease was added instead of 0.64 µL. Therefore, the final concentration of the Gibson reaction mix was the following: 100 mM Tris-HCl PH7.5, 10 mM $MgCl_2$, 0.2 mM each dNTP, 10 mM DTT, 5% PEG-8000, 1 mM NAD, 7.5 U/mL T5 exonuclease, 25 U/mL Phusion polymerase, 4 U/µl Taq DNA ligase, 0.02-0.5 µmol DNA fragments. This reaction mix was then incubated at 50° C. for one hour. After the isothermal assembly, the reaction was dialyzed using a 0.025 µm nitrocellulose membrane (Merck™ MF-Millipore™, Ireland), and subsequently transferred to *E. coli* TOP10 cells as a plasmid maintenance host by electroporation using Micropulser Electroporator (Bio-Rad, California, USA) in a 0.2 cm electroporation cuvette at a voltage of 2.5 kV.

The second and third construct, carries the native DAR BGC from *Photorhabdus khanii* HGB1456 (pZW-ADC5) and *Photorhabdus khanii* DSM3369 (pZW-ADC6), respectively. For both constructs, the respective BGC was amplified by PCR according to methods as are known to the person skilled in the art; therefore, the respective bacterial genomic DNA was used as template. Gibson Assembly was performed as described above.

Plasmids pZW-ADC3.2 and pZW-ADC5.2 were created by restriction-digest of pZW-ADC3 and pZW-ADC5. Each plasmid was restricted using NcoI and NotI (New England Biolabs, Ipswich, USA). Then, an additional codon optimized version of *Photorhabdus* sp. darA (SEQ ID NO: 26) was inserted into the first multiple cloning site of the pRSFDuet™-1 based vectors by Gibson Assembly.

The plasmids pZW-ADC7 and pZW-ADC8 carry the native DAR BGC from *P. khanii* HGB1456 with an additional 200 bp and 605 bp upstream region of darA, respectively. The BGCs were amplified from the bacterial genomic DNA by PCR according to methods as are known to the person skilled in the art. The respective inserts were assembled to the NdeI-AvrII linearized pRSFDuet™-1 using Gibson Assembly.

The plasmid pZW-ADC9 carries the DAR BGC from *P. khanii* DSM3369 without the transporter genes, i.e. only darA and darE. Both fragments were amplified by PCR and assembled to the NdeI-AvrII linearized pRSFDuet™-1 using Gibson Assembly.

pZW-YerA4 carries the DAR BGC derived from *Yersinia frederiksenii* ATCC 33641 that was amplified by PCR. The amplificate was also assembled to the NdeI-AvrII linearized pRSFDuet™-1 by using Gibson assembly.

Following assembly and propagation in *E. coli* TOP10 cells, all constructs were checked by test PCR and by their restriction pattern.

The DAR resistant strain was generated by introduction of three point mutation into the bamA gene, which are 1300A>G, 1334A>C, and 2113G>A. That these three point mutations result in a DAR resistant phenotype was confirmed by a previous study, whereby DAR resistance increased to 128 µg/mL. This previous study is known to the person skilled in the art. Mutations to create a resistant producer strain can be generated by procedures well known by the person skilled in the art. The gene to be modified for this purpose can be—for example—bamA.

The expression constructs were transferred from the maintenance host, *E. coli* TOP10, into different expression hosts by electroporation. The transformation of *E. coli* expression hosts was performed as described above for *E. coli* TOP10, while the transformation of V. *natriegens* Vmax™ was done in a 0.1 cm electroporation cuvette at a voltage of 900 V. After the electroporation, the strains were incubated for 1 hour in their respective growth medium and temperature. Then, they were plated on LB(-ASW) plates containing kanamycin as the selective agent with the aforementioned concentration, with the addition of chloramphenicol when *E. coli* Rosetta™ (DE3) was used as the host. Single colonies were picked from the selective plates and the presence of the respective expression plasmid was confirmed by PCR. Colonies with correct constructs were then inoculated in 3 mL LB(-ASW) containing required antibiotics and incubated at 37° C. or 30° C. overnight. 500 µL of this pre-culture were used to inoculate 50 ml of fresh LB(-ASW) medium containing kanamycin, incubated at 37° C. or 30° C. until an $OD_{600}$ of 0.4-0.6 was reached, and then induced with IPTG (final concentration of 0.5 mM). After IPTG induction, the cultures were incubated at 30° C. with 180 rpm shaking. The person skilled in the art knows that if an inducible promoter is used for expression one can use non-resistant producer strains without leaving the scope of the invention, because expression can be induced when a certain cell density is reached. Thereby the cells are not killed by the production of the antibiotic.

DAR production was analyzed by UPLC-HRMS. From the expression culture, a 1 mL aliquot was taken and centrifuged to separate the medium and the bacterial cell. The medium was lyophilized, 1 mL methanol was added, the mixture was sonicated in a Bandelin Sonorex RK255 ultrasonic bath (Berlin, Germany) for 30 minutes, and centrifuged at 10,000 g for 5 minutes. The methanol was removed, and the pellet was resuspended in 1 ml deionized water. After a final centrifugation at 10,000 g for 5 minutes, the sample was ready to be injected to the UPLC-HRMS system. To prepare the sample from the cell pellet, 500 µL of methanol was added prior to sonication for 30 minutes. Then, 500 µL of deionized water was added, and the sonication was continued for another 15 minutes. Thereafter, the solution was centrifuged to pellet the insoluble part and the supernatant was injected to the UPLC-HRMS system.

The UPLC-HRMS system was an Agilent Infinity 1290 UPLC system equipped with an Acquity UPLC BEH C18 1.7 µm (2.1×100 mm) column (Waters, Eschborn, Germany) and an Acquity UPLC BEH C18 1.7 µm VanGuard Pre-Column (2.1×5 mm; Waters, Eschborn, Germany) setup coupled to a DAD detector and a micrOTOFQ II mass spectrometer (Bruker, Bremen, Germany). The LC part was run using a gradient (A: $H_2O$, 0.1% FA; B: MeCN, 0.1% FA; Flow: 600 L/min): 0 min: 95% A; 0.80 min: 95% A; 18.70 min: 4.75% A; 18.80 min: 0% A; 23.00 min: 0% A; 23.10 min: 95% A; 25.00 min: 95% A and the column oven temperature was set to 45° C. MS parameters were as follows: nebulizer gas 1.6 bar; gas temperature, 200° C.; gas flow, 8 L/min; capillary voltage, 4500 V; endplate offset, 500 V; measurement was done in positive ion mode.

A DAR standard curve was generated by plotting the peak area of DAR from the extracted ion chromatogram (EIC) (for the m/z of 483.7089 and 475.1956+0.01) to a series of DAR concentrations (2, 3, 4, 5, 10, 15, 20, 30, 40 mg/L). The DAR concentration from a heterologous expression culture was quantified by calculating the peak area and interpolating it to the DAR standard curve. The linear range for this quantification method was 3 µg/mL to 30 µg/mL. Therefore, the peak area below the border was not converted to concentration. The standard curve was measured with all batches that were analyzed by UPLC-HRMS to exclude technical differences between measurements.

The three genes darB, darC and darD are coding for subunits of an ABC transporter. To answer the question whether these transporter genes play an additional role to the biosynthesis of DAR and to define the minimum DAR BGC, these genes were removed from the expression construct. Therefore, pZW-ADC9, a construct that carries only darA and darE, was created. This experiment showed that without darBCD, DAR could still be produced. Furthermore, DAR was detected outside of the cell.

It was evaluated if the transporter-encoding genes darBCD are essential for the heterologous DAR expression or if darA, encoding the precursor peptide and darE, encoding the radical SAM modification enzyme, are sufficient. Deletion of darBCD did not abolish DAR production. However, the yield was lower (1.5-fold) than the one reached with the construct including transporter genes (pZW-ADC6). Most interestingly, DAR was also present in the medium, even without the transporter-encoding genes. On the one hand, this clearly defines the minimum DAR BGC, which consists of only darA and darE. On the other hand, it became clear that in *E. coli* DAR is present outside the cell even without the specific heterologous transporter genes darBCD.

Heterologous Expression of Other Bicyclic Heptapeptides

Based on expression constructs as exemplified above, the amino acids of the heptapeptide can be exchanged. This can be done specifically for individual amino acids, or in a randomized approach using primers to modify the sequence of the heptapeptide. Therefore, specific or degenerated primers (e.g., using the triplet NNN or NNK for any proteinogenic amino acid to be incorporated at a given position) were designed to modify one or more amino acids of the core (=hepta) peptide. As example, a suitable PCR mix for a 50 µL scale reaction contained: Water: 34-34.5 µL, DMSO: 2.5 µL, Q5 reaction buffer: 10 µL, dNTPs: 1 µL, forward primer (100 pmol/µL): 0.5 µL, reverse primer (100 µmol/µL): 0.5 µL, template DNA: 0.5 µL, Q5 DNA polymerase: 0.5-1 µL. The PCR program can be as follows: step1 98° C., 10 min; step 2 98° C., 10 sec; step 3 65° C., 20 s; step 4 72° C., 7 min; 30 cycles step 2-4); step 5 72° C., 10 min; step 6 4° C.,∞.

In that way, all possible combinations of amino acids according to formula I can be incorporated into the heptapeptide. Furthermore, these derivatives can also be halogenized or modified by the presence of a double bond, according to formula I.

Structure Elucidation

All NMR data were recorded on a Bruker Avance III HD 600 MHz NMR spectrometer (Bruker BioSpin MRI GmbH, Ettlingen, Germany). For all NMR experiments, deuterium oxide (Deutero GmbH, Kastellaun, Germany) was used as solvent. $^1$H NMR spectra were referenced to the solvent residual peak according to the literature. For referencing of $^{13}$C spectra 3-trimethylsilyl-d4-propionic acid (TSPA) was employed as an external standard as is known to the person skilled in the art. Complete assignments were obtained using 2D experiments including COSY (cosygpmfphpp), TOCSY (mlevetgp and mlevgpph19), $^1$H-$^{13}$C_HSQC (hsqcedetgp-sisp2.3), and $^1$H-$^{13}$C_HMBC (hmbcetgpl3nd). To improve resolution of 1H-$^{13}$C_HMBC spectra, additional experiments were performed using non-uniform sampling (NUS) and/or $H_2O$ suppression. $H_2O$ suppression was also applied for the recording of TOCSY spectra. Analysis of NMR spectra was performed using the software TopSpin 3.6.0 (Bruker BioSpin MRI GmbH, Ettlingen, Germany).

Identification of Biosynthetic Gene Cluster

A direct screening for the core peptide sequence WNWSKSF (SEQ ID NO: 38) was done on all *Photorhabdus* genomes available in public databases using Basic Local Alignment Search Tool (BLAST). In *P. temperata* the seven amino acid sequence of darobactin was located close to the C-terminus of an open reading frame coding for 58 amino acids, upstream of an ABC transporter and a radical SAM enzyme, suggesting a RiPP operon. This putative BGC was identified in the other darobactin producers, e.g. *P. luminescens* DSM-3368 and *P. khanii* DSM-3369. The boundaries of the cluster were determined by comparison with the *P. bodei* genome, which did not contain the operon. Furthermore, the GC content of the dar cluster was clearly lower than the rest of the average GC content in the genome (32% vs 45%). In order to identify other bacterial species that potentially produce darobactin-like compounds, homologous enzymes were searched using the radical SAM protein sequence (DarE) as input in BLAST. The genomic context of each hit was analyzed manually to confirm the presence of a DarA-like propeptide in the vicinity of the radical SAM protein. In addition, a search using the propeptide DarA as input was done, delivering the same hits.

Generation of a Darobactin Deletion Mutant and Heterologous Expression

To delete the dar BGC (darABCDE) from the genome of the producer strain *Photorhabdus khanii* DSM3369, a plasmid was constructed by assembly of 5 fragments, which enables marker less genome modification. Therefore, chromosomal DNA was isolated using the innuprepBacteria DNA Kit (AnalytikJena, Jena, Germany).

Fragments (i) up- and (ii) downstream of the BGC were amplified (size ~1 kb) using the primer pairs (SEQ ID NO: 1):
5'-TTTGACGTTGGAGTCCACGTGT-TATGGACGTGGCAAACGGGGTTCTTGAC-3', and (SEQ ID NO: 2):
5'-TTGAAATATCAGGATAGCATTGCGCTCGCT-CACCCCGGTCACATAGTTCG-3', as well as (SEQ ID NO: 3):
5'-ATGCTATCCTGATATTT-CAAATGCAAGTAAAATGTTTCATCAT-AATAACC-3' and (SEQ ID NO: 4):
5'-TTCTTGACGAGTTCTTCTGAGATGGGTTGA-TATCCACTGATATAAATCTC-3'. (iii) The R$^6$K origin of replication (ori), the origin of transfer (oriT) and the levan sucrase gene sacB from *Bacillus subtilis* were amplified in one piece from the vector pNPTS138 using the primers (SEQ ID NO: 5):
5'-TCGAGCTCTAAGGAGGTTATAAAAAATGAA-CATCAAAAAGTTTGCAAAACAAG CA-3' and (SEQ ID NO: 6): 5'-ACGTGGACTCCAACGT-CAAA-3'. (iv) The arabinose inducible expression system of pKD46 with the adjacent beta-lactamase (bla) promoter was amplified using the primers (SEQ ID NO: 7):
5'-ACTCTTCCTTTTTCAATATTATTGAAGCAT-3' and (SEQ ID NO: 8):
5'-TGCATTTTTTATAACCTCCTTAGAGCTCGAAT-TCC-3', and (v) the aph gene from pCAP03 conferring resistance to kanamycin, was amplified using the primers (SEQ ID NO: 9):
5'-TCAGAAGAACTCGTCAAGAAGGCGA-3' and (SEQ ID NO: 10):
5'-TCAATAATATTGAAAAAGGAAGAGTATGATT-GAACAAGATGGATTGCACG-3'.

All fragments were amplified by Q5 DNA polymerase (New England Biolabs, Ipswich, USA), gel purified with 1% or 2% TAE agarose gels and DNA was retrieved with the Large Fragment DNA Recovery Kit (Zymo Research, Irvine, USA).

Subsequently all fragments were fused by isothermal assembly, generating the plasmid pNB02. After assembly, *E. coli* WM3064 cells were transformed with pNB02 by electroporation and correct assembly was corroborated by PCR and restriction analysis following standard procedures. Conjugation between *E. coli* WM3064 and *P. khanii* DSM3369 was performed by growing both strains to an OD$_{600}$ of ~0.6. After washing twice with LB medium, cells were mixed in 1:3 ratio of *E. coli* and *P. khanii*, plated out on LB agar supplemented with diaminopimelinic acid (0.3 mM) and incubated at 37° C. for 3 h, followed by overnight incubation at 30° C. The bacterial lawn was resuspended in LB medium and plated on LB agar with kanamycin (50 μg ml$^{-1}$) in serial dilution. Kanamycin resistant single cross over transconjugants were grown in LB medium to an OD$_{600}$ of ~0.6. Then, expression of SacB was induced by adding arabinose (0.2% w/v), followed by 2 h incubation.

Subsequently, the culture was plated out on LB agar supplemented with 0.2% (w/v) arabinose and 10% sucrose and incubated at 30° C. for 48 h. Single colonies were picked on LB$_{Kan}$ and LB$_{Ara/Suc}$ agar. Sensitivity to kanamycin indicated plasmid loss and therewith a successful double crossover event. Clones were picked and analyzed for BGC loss by PCR using the primers (SEQ ID NO: 11):
5'-ATCTCCATCAAAGCGCTACC-3' and (SEQ ID NO: 12): 5'-CCGCGCTGCAACTCGAAATC-3'.

The knock out strain is called *P. khanii* DSM3369 ΔdarABCDE.

For heterologous expression of the darobactin A BGC in *E. coli* and to complement *P. khanii* DSM3369 ΔdarABCDE, the expression plasmid pNB03 was used. To avoid issues with the regulation system between the propeptide and the modifying enzymes, all intergenic regions were removed and the genes darA-darE were expressed streamlined under the control of the arabinose inducible araB promoter. pNB03 was created by amplification of (i) the p15A ori from pACYC177 (primers (SEQ ID NO: 13):
5'-GGTCGACGGATCCCCGGAATAGCG-GAAATGGCTTAGGAAC-3' and (SEQ ID NO: 14):
5'-CTCTAAGGAGGTTATAAAAAGCGGCCG-CATCCCTTAACGTGAGTTTC-3'),
(ii) the arabinose expression system and kanamycin resistance of pNB02 (primers (SEQ ID NO: 15):
5'-AAGCAGCTCCAGCCTA-CATCAGAAGAACTCGTCAAGAAGGCGA-3' and (SEQ ID NO: 16):
5'-TTTTTATAACCTCCTTAGAGCTCGAATTCC-3'),
as well as (iii) the oriT and the aac(3) gene conferring resistance to apramycin from pIJ773 (primers (SEQ ID NO: 17): 5'-ATTCCGGGGATCCGTCGACC-3' and (SEQ ID NO: 18): 5'-TGTAGGCTGGAGCTGCTT-3').

Subsequently, all fragments were gel purified and assembled as described previously. *E. coli* TOP10 cells were transformed with the vector and correct assembly was corroborated.

To introduce the dar BGC into *P. khanii* DSM3369 ΔdarABCDE, (i) pNB03 was linearized using the primers (SEQ ID NO: 19): 5'-TCCCTTAACGTGAGTTTTCG-3' and
(SEQ ID NO: 20): 5'-TTTTATAACCTCCT-TAGAGCTCGAA-3'
  (ii) darA was amplified using (SEQ ID NO: 21): 5'-GCTCTAAGGAGGTTATAAAAATGCATAATACCT-TAAATGAAACCGTTAAA-3' and (SEQ ID NO: 22): 5'-AATAGCATTCATTTATGGCTCTCCTTTTAAAT-TTCCTGGAAGCTTT-3', (iii) darB-darE were ampli-fied using (SEQ ID NO: 23): 5'-AAAGCTTCCAG-GAAATTTAAAAGGAGAGCCATAAATGAATG-CTATT-3' and
(SEQ ID NO: 24): 5'-CGAAAACTCACGTTAAGGGATTACGCCGC-GATGGTTTGTTTTATT-3'.

All fragments were gel purified and assembled as described above. The resulting vector pNB03-darABCDE was transferred to *E. coli* TOP10 cells and correct assembly was corroborated.

The empty pNB03 as well as pNB03-darABCDE were transferred to *P. khanii* DSM3369 ΔdarABCDE by triparental conjugation. In brief, conjugation between *P. khanii* DSM3369 ΔdarABCDE, *E. coli* TOP10 carrying the expression plas-mid and *E. coli* ET pUB307, harboring the pUB307 conju-gation helper plasmid was carried out as before (cell ratio 3:1:1). Since *P. khanii* DSM3369 is naturally resistant to carbenicillin and the kanamycin resistance of pUB307 lacks the bla promoter, final selection took place on LB agar supplemented with kanamycin and carbenicillin. Kanamy-cin resistant transconjugants were grown in LB$_{Kan}$, the plasmid was isolated and the identity verified by PCR. For heterologous expression, the vector pNB03-darABCDE was transferred in *E. coli* BW25113 (arabinose non-utilizer) by electroporation. Subsequently, *P. khanii* DSM3369 WT, *P. khanii* DSM3369 ΔdarABCDE+pNB03, *P. khanii* DSM3369 ΔdarABCDE+pNB03-darABCDE, and *E. coli*+ pNB03-darABCDE were grown in LB or LB$_{Kan}$ supple-mented with 0.2% (w/v) arabinose for 5-7 days and analyzed by LCMS.

Minimum Inhibitory Concentration (MIC)

The MICs were determined by microbroth dilution assays in round bottom 96-well plates. Overnight cultures of *E. coli* ATCC35218, *E. coli* NRZ14408 KPC-2, *E. coli* K0416 VIM-1, *E. coli* Survcare 052 NDM-5, *E. coli* MMGI1 OXA-48, *P. aeruginosa* PAO 1, *P. aeruginosa* PAO 750, *A. baumanii* ATCC19606, *K. pneumoniae* ATCC30104 and *S. enterica* ATCC13076 were adjusted to McFarland 1.0 and subsequently diluted to 5×10^5 c.f.u. mL$^{-1}$ in MHIIB. Daro-bactin derivatives were screened in 12 concentrations rang-ing from 64 to 0.03 μg mL$^{-1}$ in triplicate. The same con-centrations were tested for rifampicin, tetracycline and gentamycin as positive controls. For tetracycline resistant *E. coli* strains (NRZ14408, K0416 and MMGI1) as well as for *E. coli* Survcare 052 tetracycline was substituted with a colistin dilution series (16-0.007 μg mL$^{-1}$).

Bacteria suspension without supplemented standard anti-biotics or darobactin was used as negative control. After incubation (18h, 180 rpm, 37° C., 85% r.H.), cell growth was determined by measuring the turbidity with a microplate spectrophotometer at 600 nm. The MIC was defined as the minimum concentration where at least 85% growth inhibi-tion relative to the negative control was measured.

The Invention Claims:

The invention comprises several aspects, closely con-nected to each other. All-encompassing is the claim for bicyclic heptapeptides, their manufacturing and usage as APIs within medical preparations resp. pharmaceutical com-positions. The expressions "medical preparation" and "phar-maceutical composition" are used synonymously herein.

DESCRIPTION OF THE DRAWINGS

FIG. 1A, DAR is a modified heptapeptide consisting of the seven amino acids W$^1$—N$^2$—W$^3$-S$^4$-K$^5$-S$^6$—F$^7$ (SEQ ID NO: 38), with an ether bond between W$^1$ and W$^3$, and a C—C bond between W$^3$ and K$^5$. FIG. 1B, The dar BGC (in total 6.2 kb in length) consists of darA that encodes the precursor peptide; darBCD that encode subunits of an ABC transporter; and darE that encodes a radical S-adenosylmethionine enzyme (RaS).

Figure 2B:
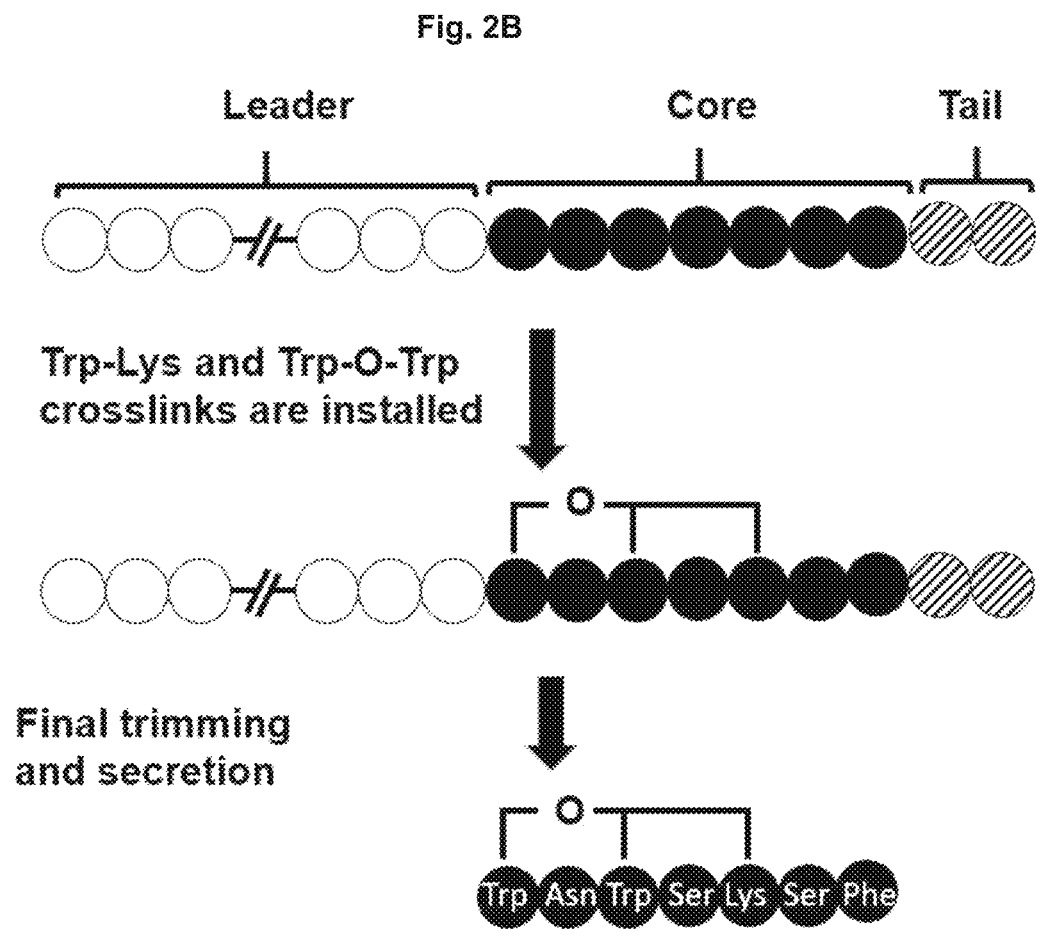

FIGS. 2A-C Biosynthetic Gene Cluster (BGC) of Daro-bactin in Selected Bacterial Strains.

FIG. 2A, The BGC consists of the structural gene darA, darBCD (transporter encoding genes) and darE (encoding a radical SAM enzyme). In addition a relE-like gene ORF can be co-located with the BGC at different positions. The BGC can be detected in most *Photorhabdus* strains in a conserved genetic region. In addition, homologous BGCs (related genes) are in *Yersinia, Vibrio* and *Pseudoalteromonas* strains. FIG. 2B, Biosynthetic hypothesis. The propeptide encoded by darA consists of 58 amino acids. The crosslinks are installed on the linear propeptide by DarE.

In a next step the leader and tail regions are cleaved off and darobactin is secreted by the ABC transporter DarBCD. FIG. 2C, Amino acid sequence of the propeptide from selected bacterial strains. The darobactin core peptide is highlighted in bold and the amino acids involved in the crosslinking. The star indicates the stop codon. (SEQ ID NO: 31) is darA from *Photorhabdus* temperata, (SEQ ID NO: 32) is darA from *Photorhabdus* khanii, (SEQ ID NO: 33) is darA from *Photorhabdus australis*, (SEQ ID NO: 34) is darA from *Photorhabdus* laumondii, (SEQ ID NO: 35) is darA from *Yersinia frederiksenii*, (SEQ ID NO: 36) is darA from *Vibrio* tasmaniensis, (SEQ ID NO: 37) is darA from *Pseudoalteromonas luteoviolacea*. The boxes are showing the consensus sequences from the microorganisms forming a typical heptapeptide according to formula I.

Figure 3:
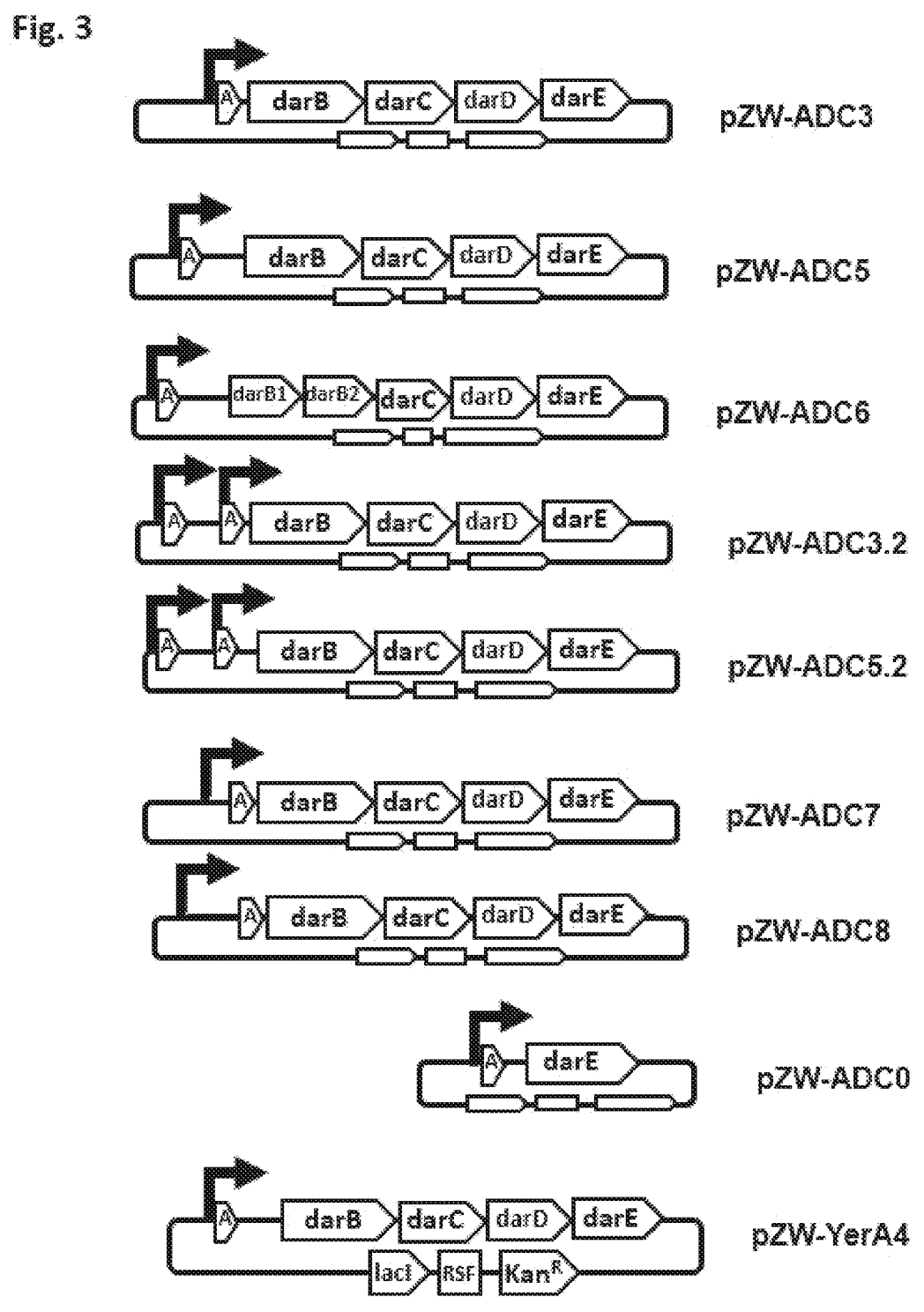

FIG. 3: Expression constructs created in this study. The DAR BGC was cloned into the pRSFDuet™-1 vector under control of the T7lac promoter. pZW-ADC3 has a streamlined DAR BGC from *P. khanii* HGB1456, where all intergenic regions were removed, while pZW-ADC5 and pZW-ADC6 carry the native cluster from *P. khanii* HGB1456 and *P. khanii* DSM3369, respectively. Addition of a second darA copy to pZW-ADC3 and pZW-ADC5 created pZW-ADC3.2 and pZW-ADC5.2. Plasmid. pZW-ADC7 carries the *P. khanii* HGB1456-derived DAR BGC with an additional 200 bp upstream region of darA and pZW-ADC8 harbors a 605 bp upstream region. Plasmid pZW-ADC9 harbors the *P. khanii* DSM3369-derived DAR BGC, omitting darBCD;

and pZW-YerA4 carries the DAR BGC from *Yersinia frede`riksenii` ATCC 33641. The black arrow indicates the T7lac promoter and for lacI, RSF and the kanamycin resistance cassette (Kan$^R$) is kept constant. The lacI gene encodes for the lac operon repressor and RSF is an origin of replication that was derived from RSF1030, which allows the plasmid to be maintained at a high copy number in the cell.

FIG. 4: NMR chemical shifts (ppm) and additional NMR-experimental data for darobactin B.

Figures 1A, 1B:
FIGS. 1A-B: Darobactin (DAR) is a ribosomally synthe-sized and post-translationally modified peptide (RiPP), encoded by the dar operon.
Figure 2A:
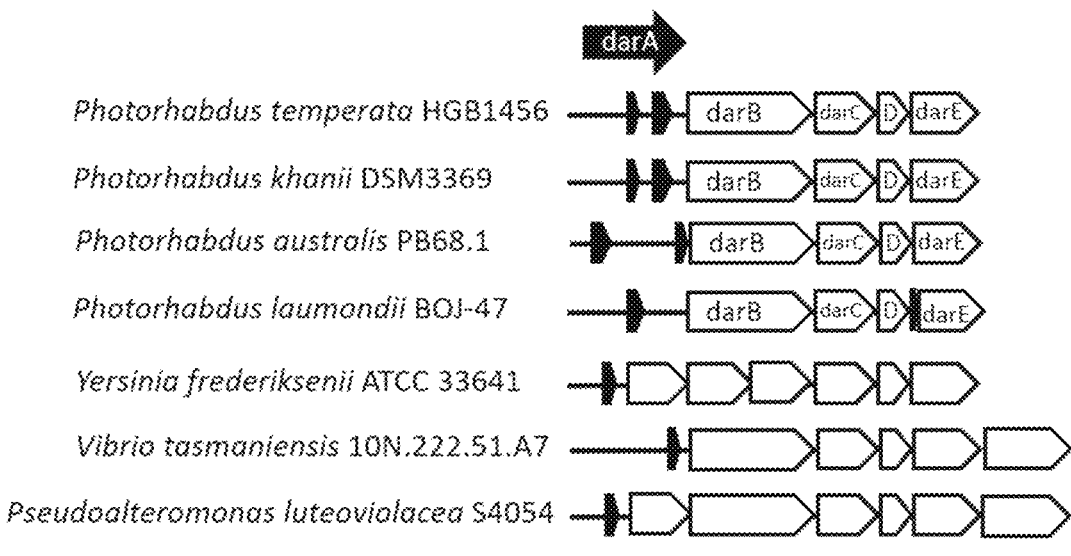
Figure 5A:
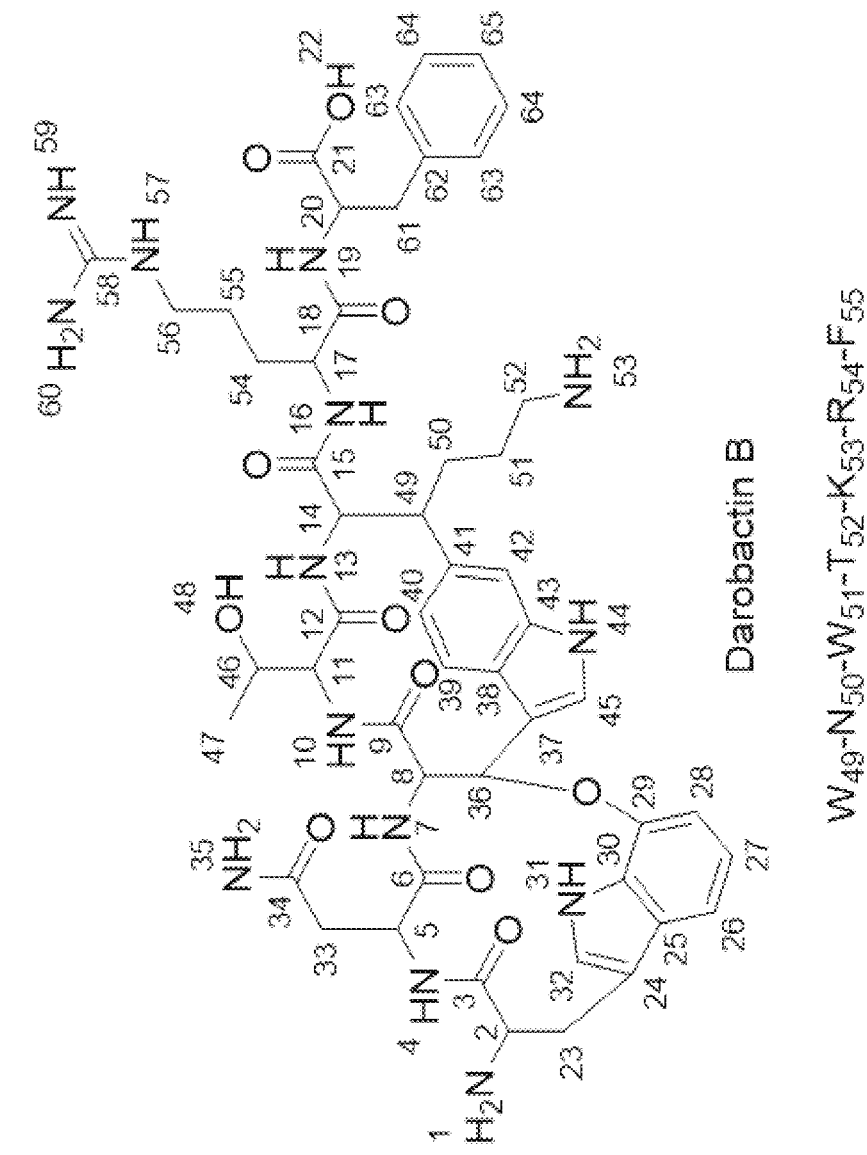

FIG. 5A: NMR assignments of darobactin B. Structure of darobactin B with numbering for NMR assignments.

Figure 5B:
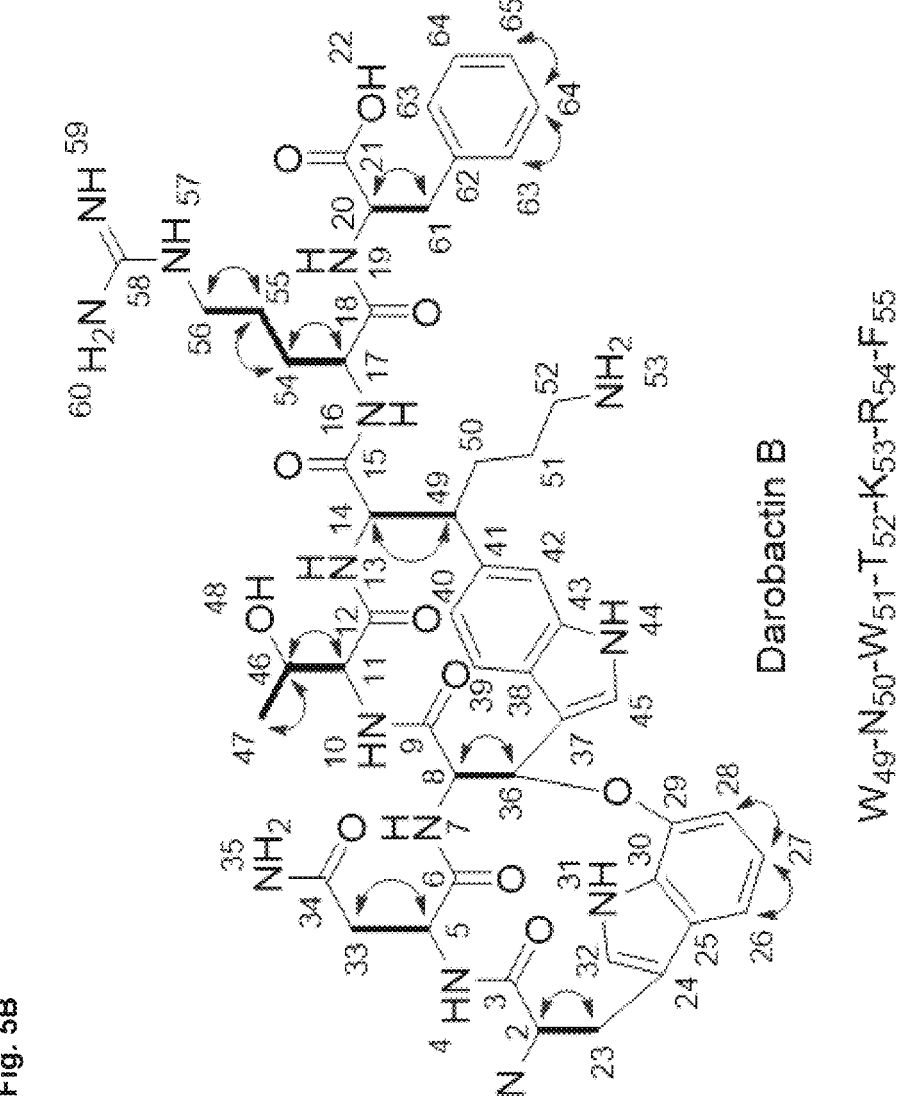

FIG. 5B: NMR assignments of darobactin B. Key COSY and TOCSY correlations (bent double-arrows indicating COSY-correlations and thick bonds indicating TOCSY-correlations).

Figure 5C:
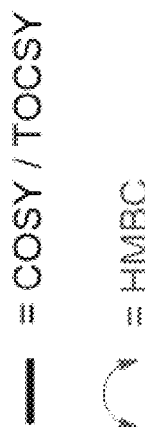
Figure 5C:
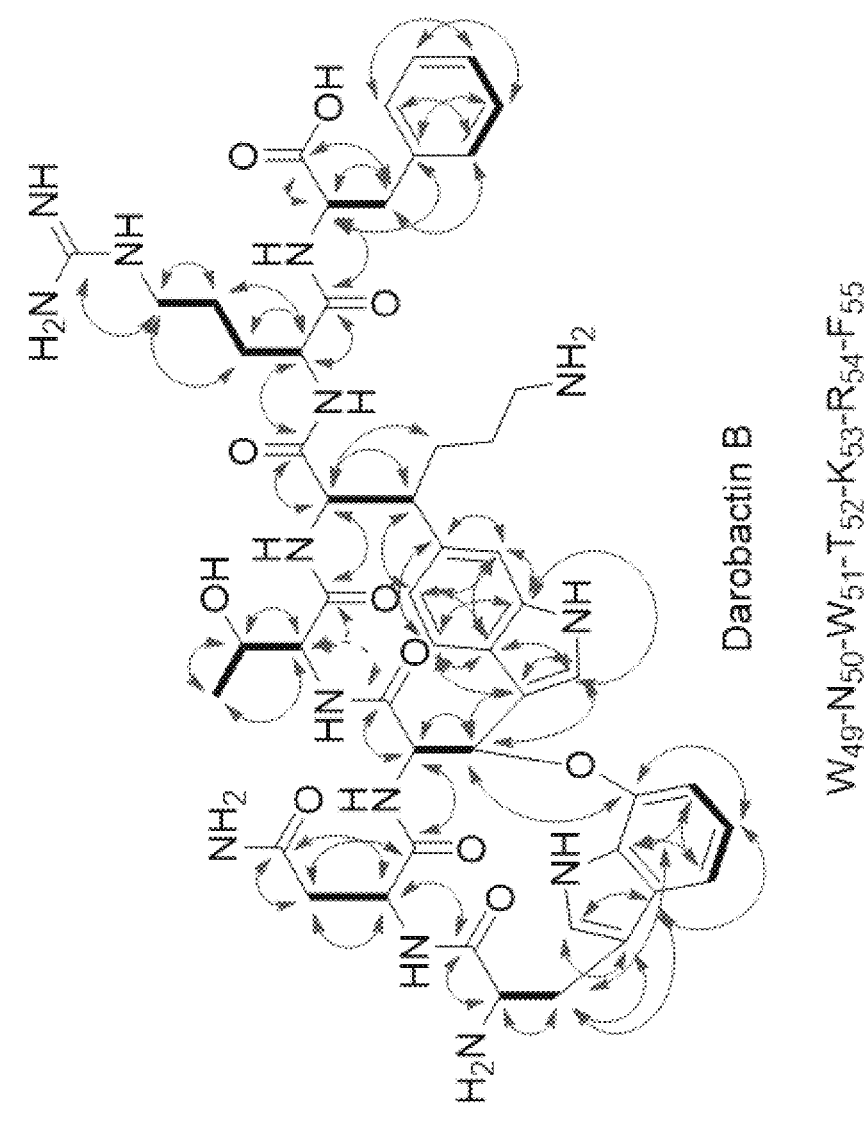

FIG. 5C: NMR assignments of darobactin B. Key HMBC correlations (bent double-arrows indicating HMBC-correlations and thick bonds indicating COSY/TOCSY-correlations).

Figure 6:
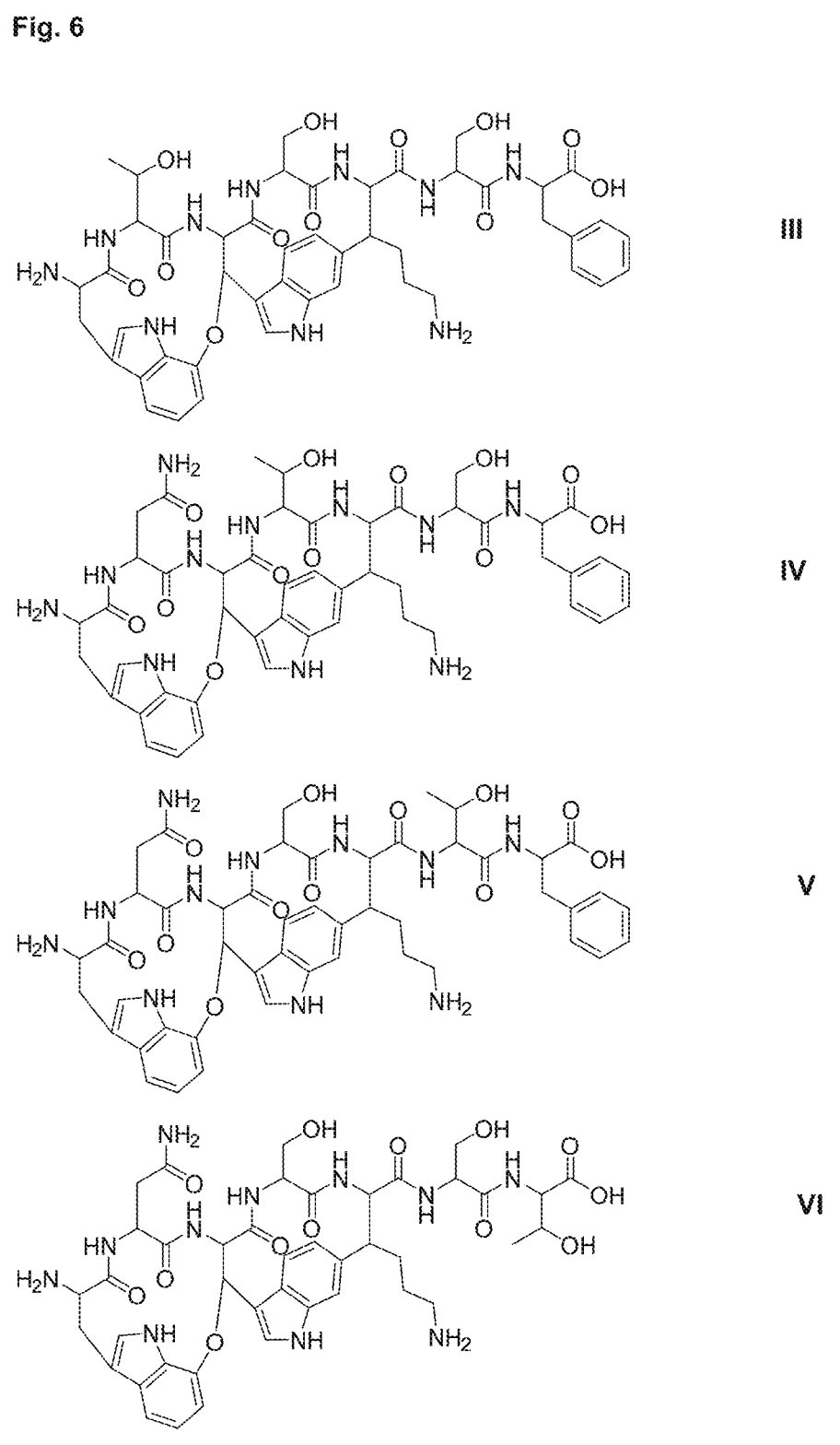

FIG. 6: Additionally exemplarily presented bicyclic heptapeptides according to the invention; not to be understood as limiting the scope of the invention (bicyclic heptapeptides III-VI).

Figure 7:
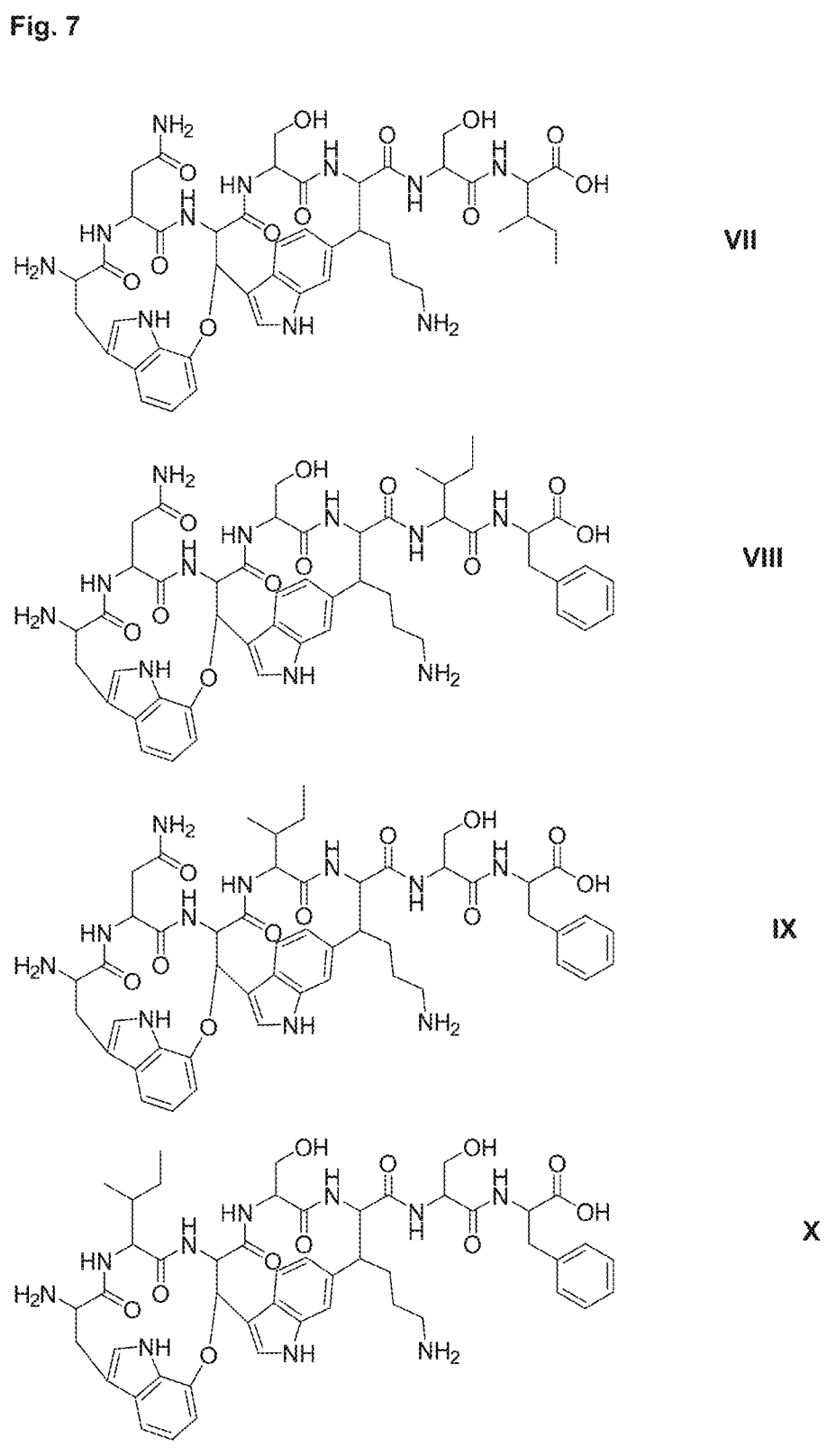

FIG. 7: Additionally exemplarily presented bicyclic heptapeptides according to the invention; not to be understood as limiting the scope of the invention (bicyclic heptapeptides VII-X).

Figure 8:
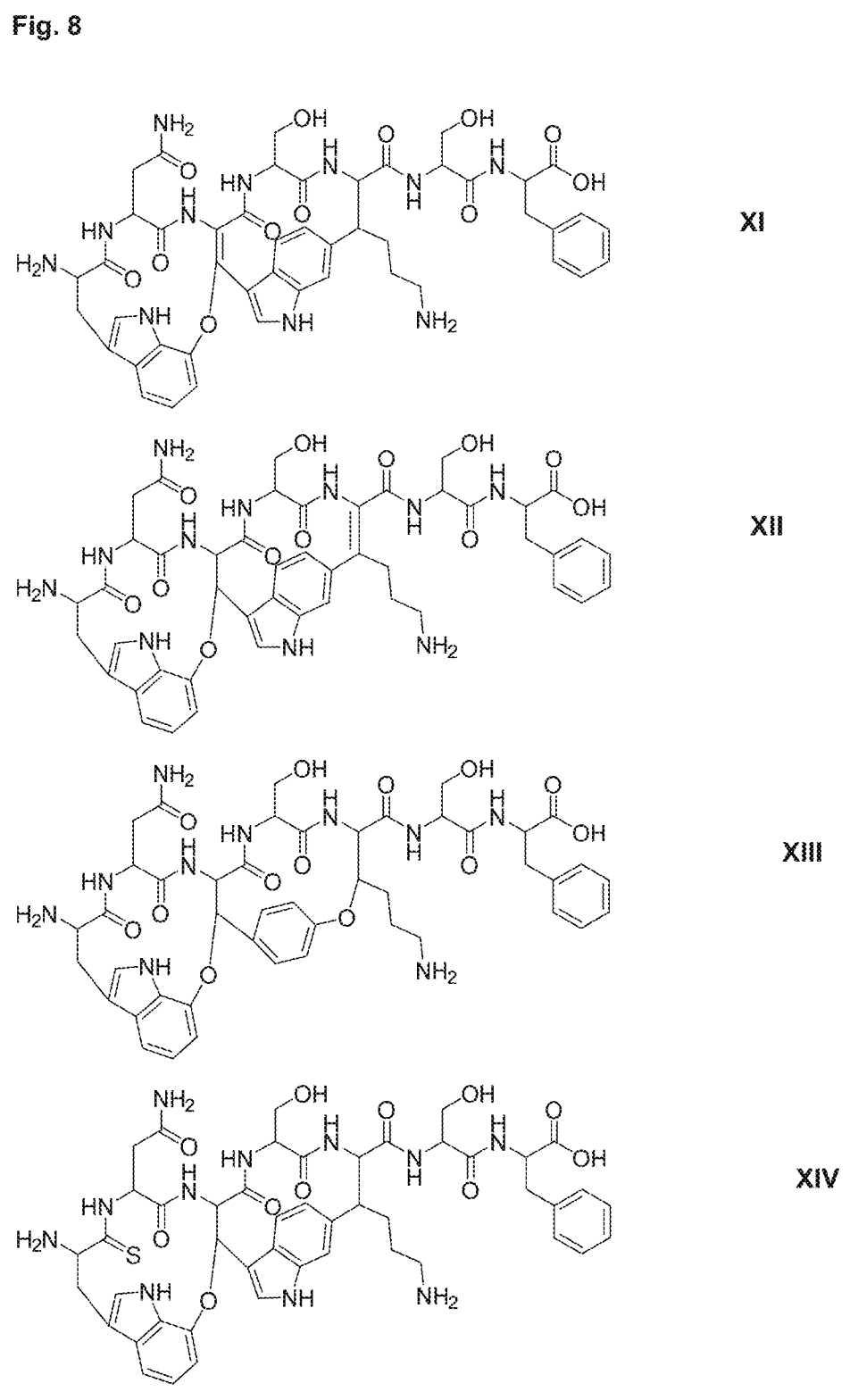

FIG. 8: Additionally exemplarily presented bicyclic heptapeptides according to the invention; not to be understood as limiting the scope of the invention (bicyclic heptapeptides XI-XIV).

Figure 9:
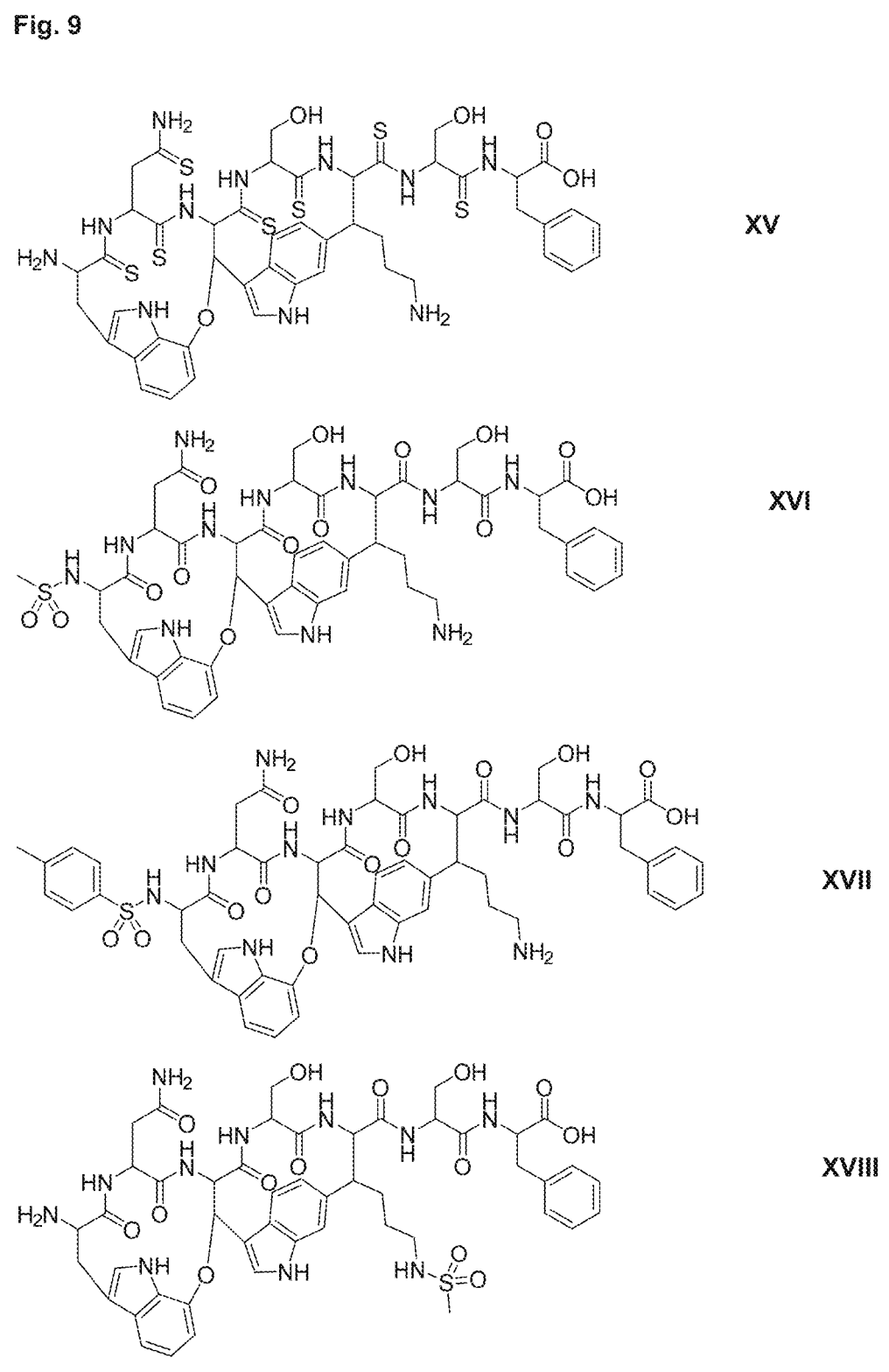

FIG. 9: Additionally exemplarily presented bicyclic heptapeptides according to the invention; not to be understood as limiting the scope of the invention (bicyclic heptapeptides XV-XVIII).

Figure 10A:
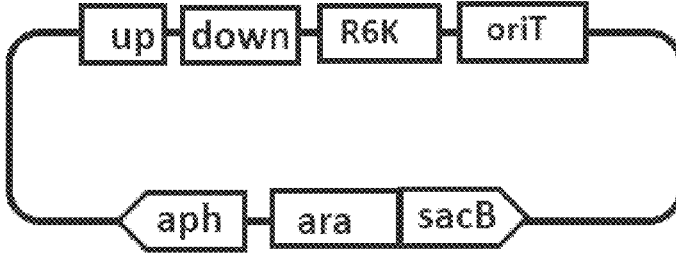
Figure 10A:
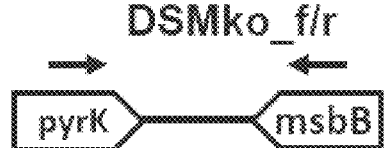
Figure 10B:
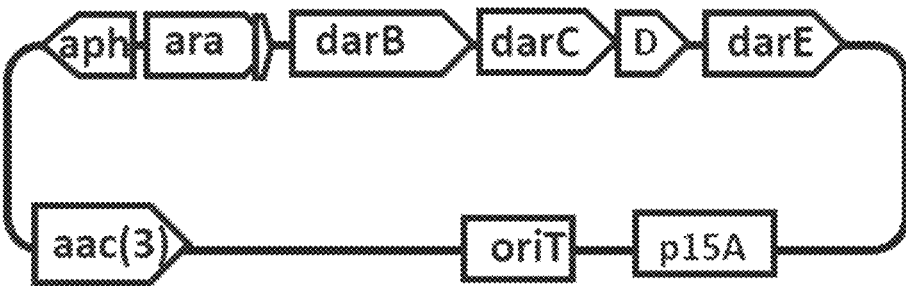

FIGS. 10A-F Darobactin knockout strain and heterologous expression, and putative structures and producers of darobactin A-E FIG. 10A, Scheme of the double cross-over knock out vector pNB02 and the targeted genomic region. FIG. 10B, Scheme of the darobactin BGC expression plasmid. FIG. 10C, Test PCRs on *P. khanii* DSM3369 ΔdarABCDE, proving the loss of the darobactin BGC; left: Amplification of darA (primers darA_f/r) resulting in a 177 bp fragment in the WT and in no fragment in the mutant; right: After loss of pNB02 (indicated by sensitivity to Kan) amplification of a 450 bp fragment if the BGC is deleted (primers DSMko_f/r); positive control: pNB03-darA-E and pNB02, respectively; primer positions in scheme a.

FIG. 10D, LC-MS extracted ion chromatogram (EIC) at m/z=483.7089±0.001, *P. khanii* DSM3369 ΔdarABCDE+pNB03, *P. khanii* DSM3369 ΔdarABCDE+pNB03-darA-E, *E. coli* BW25113+pNB03-darA-E, *P. khanii* DSM3369 WT, inset: HRMS spectrum of the ion peak showing the double charged [M+2H]$^{2+}$ion corresponding to darobactin. FIG. 10E, Putative darobactin analogs B-E were drawn based on the amino acid sequence present in the darobactin BGC. The proposed producing organisms were identified by a BLASTP search of the 7 amino acid sequence of darobactin A, and confirming the presence of darBCDE downstream of the propeptide. Amino acid changes from darobactin A. FIG. 10F, The table shows the propeptide sequence of the various darobactin analogs.

Figure 11:
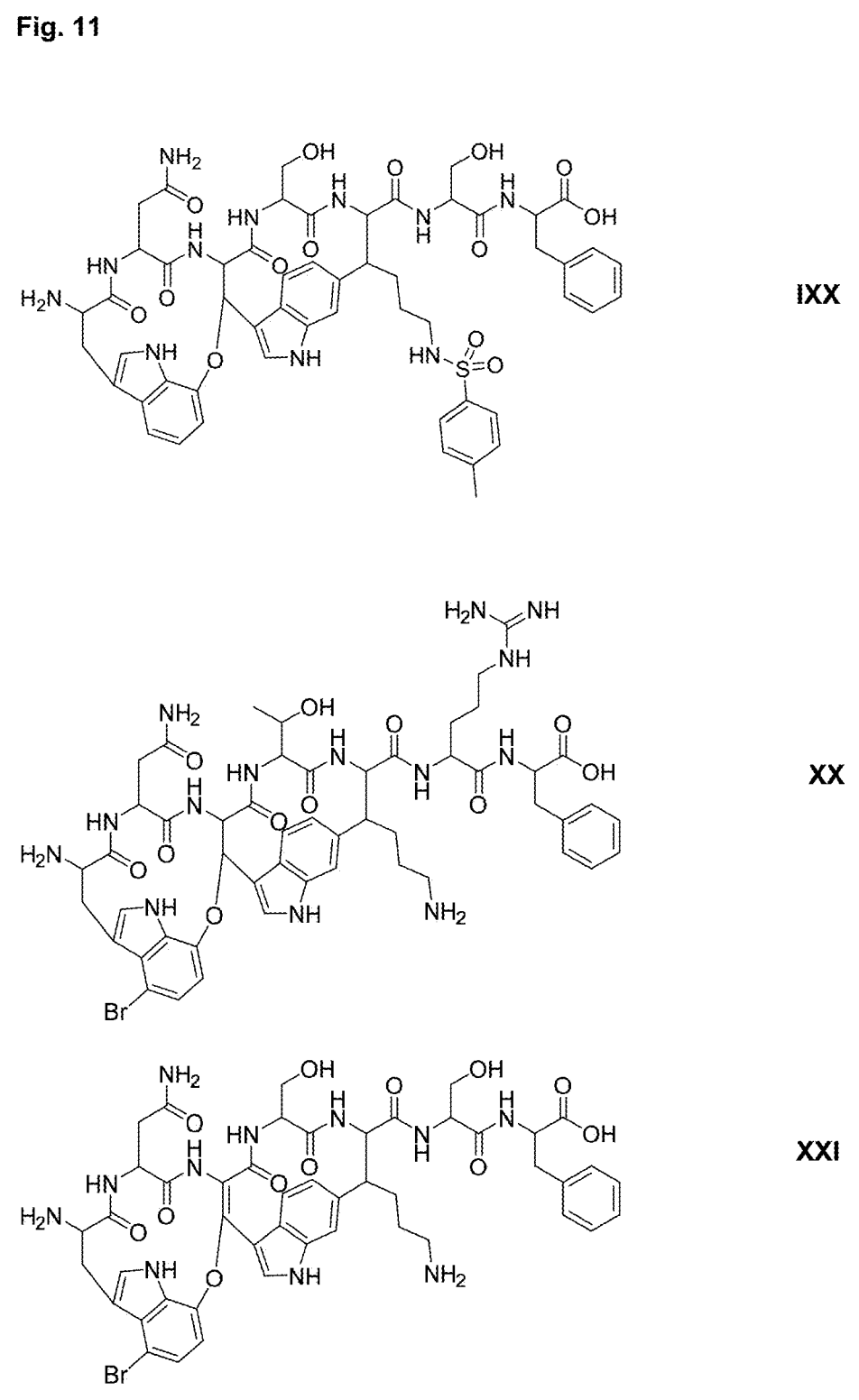

FIG. 11: Additionally exemplarily presented bicyclic heptapeptide according to the invention; not to be understood as limiting the scope of the invention (bicyclic heptapeptides IXX-XXI).

Figure 12:
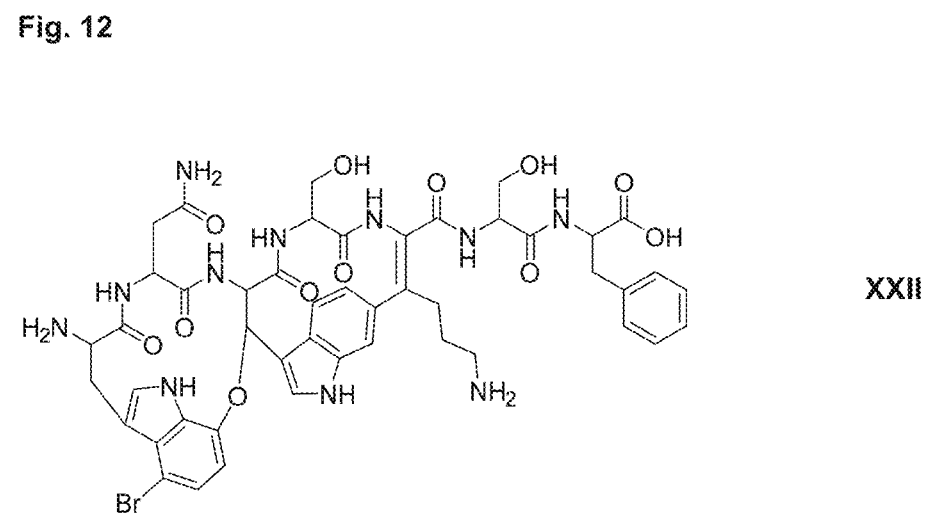

FIG. 12: Additionally exemplarily presented bicyclic heptapeptide according to the invention; not to be understood as limiting the scope of the invention (bicyclic heptapeptide XXII).

---

The invention claimed is:

1. A bicyclic heptapeptide of formula I, and/or a pharmaceutically acceptable salt, stereoisomer, tautomer or hydrate thereof, wherein $R^1$, $R^2$, $R^3$, $R^4$ are independently from each other selected from the list comprising H, —$CH_3$, —$CH_2$—$CH_2$—$CH_2$—NH—C(NH)($NH_2$), —$CH_2$—CO—$NH_2$, —$CH_2$—$CO_2H$, —$CH_2$—SH, —$CH_2$—$CH_2$—$CO_2H$, —$CH_2$—$CH_2$—CO—$NH_2$, (1H-imidazole-4-yl)-methyl, halogenated (1H-imidazole-4-yl)-methyl, —CH($CH_3$)($C_2H_5$), —$CH_2$—CH($CH_3$)$_2$, —$CH_2$—$CH_2$—$CH_2$—$CH_2NH_3$, —$CH_2$—$CH_2$—S—$CH_3$, —$CH_2$—$C_6H_5$, halogenated-$CH_2$—$C_6H_5$, (1H-indol-3-yl)-methyl, halogenated (1H-indol-3-yl)-methyl, (4-hydroxyphenyl)-methyl, halogenated (4-hydroxyphenyl)-methyl, —CH—($CH_3$)$_2$, 1-hydroxy-ethyl, hydroxy-methyl, sec-butyl, 1-acetamide, 1-thioacetamide, —$CH_2$—$CH_2$—NH—(C═NH)—$NH_2$, benzyl, halogenated benzyl, —$CH_2$—$CH_2$—$CH_2$—NH—(C═NH)—$NH_2$;

X is at any position of X independently from any other position of X either O or S;

$R^5$ is selected from the list comprising methylsulfonyl, p-toluenesulfonyl;

$R^6$ is selected from the list comprising methylsulfonyl, p-toluenesulfonyl, —(C═NH)—$NH_2$;

$Z^1$, $Z^2$ each are a double bond or a single bond in such a way that a) $Z^1$ and $Z^2$ both are single bonds or b) only one of them is a single bond and the other one is a double bond at the same time whereat i) $Z^1$ is the single bond and $Z^2$ is the double bond or ii) $Z^2$ is the single bond and $Z^1$ is the double bond;

$Y^1$ is 3,7-indolylene or halogenated 3,7-indolylene;

$Y^2$ is independently selected from the list 3,6-indolylene, 1,4-phenoxylene, halogenated 3,6-indolylene, halogenated 1,4-phenoxylene;

n is 1 or 2.

2. The bicyclic heptapeptide according to claim 1, characterized in that it is darobactin.

3. A pharmaceutical composition for treating infections in a mammal caused by Gram-negative bacteria, comprising a therapeutically effective amount of the bicyclic heptapeptide according to claim 1 or a pharmaceutically acceptable salt, solvate, or stereoisomer thereof.

4. The pharmaceutical composition according to claim 3, further comprising at least one pharmaceutically acceptable carrier, excipient or diluent.

5. The pharmaceutical composition according to claim 3, in a form of topical administration, systemic administration, parenteral administration, subcutaneous administration, or transdermal administration, rectal administration, oral administration, intravaginal administration, intranasal administration, intrabronchial administration, intraocular administration, intra-aural administration, intravenous administration, intramuscular administration, or intraperitoneal administration.

6. A method for manufacturing the bicyclic heptapeptide according to claim 1, the method comprising i) a fermentation step using a microorganism producing the bicyclic heptapeptide, the microorganism being selected from the list of microorganisms comprising *Photorhabdus* spp., *Photorhabdus laumondii*, *Photorhabdus khanii*, *Pseudoalteromonas* spp., *Pseudoalteromonas luteoviolacea*, *Pseudoalteromonas luteoviolacea*, *Yersinia* spp., *Escherichia* spp., *Vibrio* spp providing a fermentation broth containing the bicyclic heptapeptide and microbial cells;

ii) a separation step separating the fermentation broth into an unsoluble part containing microbial cells and/or debris of the microbial cells and a solution containing the bicyclic heptapeptide by means of sedimentation and/or centrifugation and/or filtration, whereat the microbial cells are destroyed or are not destroyed before applying sedimentation and/or centrifugation and/or filtration to the fermentation broth;

iii) a purification step for purification of the bicyclic heptapeptide contained within the solution from previous separation step ii), providing a solution of the purified bicyclic heptapeptide.

7. The method for manufacturing the bicyclic heptapeptide according to claim 6, characterized in that the purification step iii) of claim 6 comprises a) drying of the solution from step ii) of claim 6 by way of lyophilization and/or distillation under reduced pressure, providing a residue, b) washing the residue of previous step a) with an alcohol, drying the washed residue and solving the dried residue in deionized water providing a crude extract of the bicyclic heptapeptide, c) removing insoluble parts of the crude extract of previous step b) by means of sedimentation and/or filtration and/or centrifugation providing a solid-free crude extract, d) purifying the solid-free crude extract from previous step c) by means of chromatography, thus providing a pure solution of the bicyclic heptapeptide.

8. The method according to claim 6, characterized in that the purification step iii) of claim 6 comprises a) bringing the solution from step ii) of claim 6 into contact with a hydrophobic interaction material, so that the bicyclic heptapeptide is adsorbed to the hydrophobic interaction material, b) separating the remaining clear solution from the hydrophobic interaction material and washing the hydrophobic interaction material loaded with adsorbed bicyclic heptapeptide with water, c) eluting the bicyclic heptapeptide from the hydrophobic interaction material with a mixture of water and organic solvent, the organic solvent being selected from the list comprising MeOH, MeCN, THF, acetone, ethanol, propanol, whereat the mixture of water and organic solvent may or may not contain an acid in an amount in between 0.001% by weight until 1% by weight, d) concentrating the eluate from step c) and removing the organic solvent by applying a vacuum and bringing the now aqueous solution into contact with a strong cation ion exchange material so that the bicyclic heptapeptide is adsorbed to the cation ion exchange material, e) washing the cation ion exchange material loaded with the bicyclic heptapeptide with an acid having a concentration between 0.001% by weight until 1% by weight, f) eluting the bicyclic heptapeptide by applying an aqueous buffer solution with a pH-value from pH 5 to pH 11, collecting fractions containing the bicyclic heptapeptide, g) adsorbing the bicyclic heptapeptide from the fractions of step f) to a hydrophobic interaction material in same manner as is described in step a), h) eluting the bicyclic heptapeptide in a gradient with $H_2O$ and an organic solvent, the organic solvent being selected from the list comprising MeOH, MeCN, THF, acetone, ethanol, propanol, i) purifying the fractions containing the bicyclic heptapeptide from step h) by applying HPLC with a gradient of $H_2O$ and an organic solvent, the organic solvent being selected from the list comprising MeOH, MeCN, THF, acetone, ethanol, propanol.

9. The method according to claim 6, characterized in that the bicyclic heptapeptide is further processed by chemical modification.

10. The method for according to claim 9, characterized in that the chemical modification is reacting the bicyclic heptapeptide with Lawson's Reagent or with tosyl chloride or with mesyl chloride.

11. A method of treating a mammal suffering from a bacterial infection comprising administering to said mammal the pharmaceutical composition according to claim 3 at a frequency and for a duration sufficient to provide a beneficial effect to the mammal wherein the bacterial infection is an infection involving *Pseudomonas aeruginosa*, *Klebsiella pneumoniae*, *Acinetobacter baumannii*, and *Salmonella enteritidis*.

12. The method of claim 11 wherein the bacterial infection is an infection involving *Pseudomonas aeruginosa*, *Klebsiella pneumoniae*, *Acinetobacter baumannii*, *Neisseria gonorrhoeae*, *Chlamydia trachomatis*, *Shigella sonnei*, *Salmonella enterica Typhimurium* LT2, *Enterobacter cloacae*, *Bifidobacterium longum*, *Bacteroides fragilis*, *Lactobacillus reuteri*, *Enterococcus faecalis* and *Yersinia pestis*, *Pseudomonas*, *fluorescens*, *Pseudomonas acidovorans*, *Pseudomonas alcaligenes*, *Pseudomonas putida*, *Stenotrophomonas maltophilia*, *Burkholderia cepacia*, *Aeromonas hydrophilia*, *Escherichia coli*, *Citrobacter freundii*, *Salmonella typhimurium*, *Salmonella typhi*, *Salmonella paratyphi*, *Salmonella enteritidis*, *Shigella dysenteriae*, *Shigella flexneri*, *Enterobacter aerogenes*, *Enterobacter* spp., *Klebsiella oxytoca*, *Serratia marcescens*, *Francisella tularensis*, *Morganella morganii*, *Proteus mirabilis*, *Proteus vulgaris*, *Providencia alcalifaciens*, *Providencia rettgeri*, *Providencia stuartii*, *Acinetobacter calcoaceticus*, *Acinetobacter haemolyticus*, *Yersinia enterocolitica*, *Yersinia pseudotuberculosis*, *Yersinia intermedia*, *Bordetella pertussis*, *Bordetella parapertussis*, *Bordetella bronchiseptica*, *Haemophilus influenzae*, *Haemophilus parainfluenzae*, *Haemophilus haemolyti-*

*cus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria meningitidis, Kingella, Moraxella, Gardnerella vaginalis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus.*

13. A method of treating vertebrates or humans suffering from an infection caused by Gram-negative bacteria comprising administering to said vertebrate or human a medical preparation comprising a bicyclic heptapeptide of formula I, (I)

and/or a pharmaceutically acceptable salt, stereoisomer, tautomer or hydrate thereof, wherein $R^1$, $R^2$, $R^3$, $R^4$ are independently from each other selected from the list comprising H, $-CH_3$, $-CH_2-CH_2-CH_2-NH-C(NH)(NH_2)$, $-CH_2-CO-NH_2$, $-CH_2-CO_2H$, $-CH_2-SH$, $-CH_2-CH_2-CO_2H$, $-CH_2-CH_2-CO-NH_2$, (1H-imidazole-4-yl)-methyl, halogenated (1H-imidazole-4-yl)-methyl, $-CH(CH_3)(C_2H_5)$, $-CH_2-CH(CH_3)_2$, $-CH_2-CH_2-CH_2-CH_2NH_3$, $-CH_2-CH_2-S-CH_3$, $-CH_2-C_6H_5$, halogenated-$CH_2-C_6H_5$, (1H-indol-3-yl)-methyl, halogenated (1H-indol-3-yl)-methyl, (4-hydroxyphenyl)-methyl, halogenated (4-hydroxyphenyl)-methyl, $-CH-(CH_3)_2$, 1-hydroxy-ethyl, hydroxy-methyl, sec-butyl, 1-acetamide, 1-thioacetamide, $-CH_2-CH_2-NH-(C=NH)-NH_2$, benzyl, halogenated benzyl, $-CH_2-CH_2-CH_2-NH-(C=NH)-NH_2$;

X is at any position of X independently from any other position of X either O or S;

$R^5$ is selected from the list comprising methylsulfonyl, p-toluenesulfonyl;

$R^6$ is selected from the list comprising methylsulfonyl, p-toluenesulfonyl, $-(C=NH)-NH_2$;

$Z^1$, $Z^2$ each are a double bond or a single bond in such a way that a) $Z^1$ and $Z^2$ both are single bonds or b) only one of them is a single bond and the other one is a double bond at the same time whereat i) $Z^1$ is the single bond and $Z^2$ is the double bond or ii) $Z^2$ is the single bond and $Z^1$ is the double bond;

$Y^1$ is 3,7-indolylene or halogenated 3,7-indolylene;

$Y^2$ is independently selected from the list 3,6-indolylene, 1,4-phenoxylene, halogenated 3,6-indolylene, halogenated 1,4-phenoxylene;

n is 1 or 2 wherein the Gram negative bacteria are selected from the group *Pseudomonas aeruginosa, Klebsiella pneumoniae* and *Acinetobacter baumannii.*

\* \* \* \* \*